(12) United States Patent
Cui et al.

(10) Patent No.: US 9,309,261 B2
(45) Date of Patent: Apr. 12, 2016

(54) SPIROOXINDOLE DERIVATIVE AND PROCESS FOR PRODUCING THE SAME

(71) Applicant: OKINAWA INSTITUTE OF SCIENCE AND TECHNOLOGY SCHOOL CORPORATION, Okinawa (JP)

(72) Inventors: Hai-Lei Cui, Okinawa (JP); Fujie Tanaka, Okinawa (JP)

(73) Assignee: OKINAWA INSTITUTE OF SCIENCE AND TECHNOLOGY SCHOOL CORPORATION, Okinawa (JP)

(*) Notice: Subject to any disclaimer, the term of this patent is extended or adjusted under 35 U.S.C. 154(b) by 0 days.

(21) Appl. No.: 14/431,935

(22) PCT Filed: Oct. 4, 2013

(86) PCT No.: PCT/JP2013/077682
§ 371 (c)(1),
(2) Date: Mar. 27, 2015

(87) PCT Pub. No.: WO2014/058035
PCT Pub. Date: Apr. 17, 2014

(65) Prior Publication Data
US 2015/0246927 A1 Sep. 3, 2015

Related U.S. Application Data

(60) Provisional application No. 61/713,221, filed on Oct. 12, 2012, provisional application No. 61/717,935, filed on Oct. 24, 2012, provisional application No. 61/725,756, filed on Nov. 13, 2012, provisional application No. 61/782,831, filed on Mar. 14, 2013.

(51) Int. Cl.
*C07D 491/107* (2006.01)
*A61K 31/407* (2006.01)

(52) U.S. Cl.
CPC .................................. *C07D 491/107* (2013.01)

(58) Field of Classification Search
None
See application file for complete search history.

(56) References Cited

U.S. PATENT DOCUMENTS 6,355,648 B1   3/2002   Fensome et al.
6,391,907 B1   5/2002   Fensome et al.

FOREIGN PATENT DOCUMENTS

WO    00/66555 A1   11/2000
WO    00/66556 A1   11/2000

OTHER PUBLICATIONS

Wang, et al., Org. Lett., 13:3086 (May 18, 2011) (Supplemental Experimental Information).*
Wang et al., "Highly Stereoselective Bronsted Acid Catalyzed Synthesis of Spirooxindole Pyrans", Organic Letters, 2011, vol. 13, No. 12, 3086-3089 (Cited in ISR and mentioned in paragraph Nos. 2 and 4 of the as-filed specification.).
Anada et al., "A New Dirhodiunn(II) Carboxamidate Complex as a Chiral Lewis Acid Catalyst for Enantioselective Hetero-Diels-Alder Reactions", Angew. Chem., 2004, 116, 2719-2722 (Mentioned in paragraph Nos. 3-4 of the as-filed specification.).
Momiyama et al., "Chiral Phosphoric Acid-Governed Anti-Diastereoselective and Enantioselective Hetero-Diels-Alder Reaction of Glyoxylate", J. Am. Chem. Soc. 2009, 131, 12882-12883 (Mentioned in paragraph Nos. 3-4 of the as-filed specification.).
Castaldi et al., "Stereoselective Synthesis of Spirocyclic Oxindoles via Prins Cyclizations", Organic Letters, 2009, vol. 11, No. 15, pp. 3362-3365 (Cited in ISR.).
Yoshida et al., "Oxidation of Cycloalkan[b]indoles with Iodine Pentoxide (I2O5)", Chemical & Pharmaceutical Bulletin, 1987, vol. 35, No. 12, pp. 4700-4704 (Cited in ISR.).
Mori et al., "Organocatalytic Asymmetric Hetero-Diels-Alder Reaction of Oxindoles under High Pressure", 37, Synlett, 2011, No. 14, pp. 2080-2084 (Cited in ISR.).
Xiong et al., "Trienamine Catalysis with 2,4-Dienones: Development and Application in Asymmetric Diels-Alder Reactions", Angewandte Chemie, International Edition, 2012. 04, vol. 51, No. 18, pp. 4401-4404 (Cited in ISR.).
Cui et al., "Catalytic Enantioselective Formal Hetero-Diels-Alder Reactions of Enones with Isatins to Give Spirooxindole Tetrahydropyranones", Chemistry—A European Journal, 2013. 04, vol. 19, No. 20, pp. 6213-6216 (Cited in ISR.).
International Search Report (ISR) issued in PCT/JP2013/077682 mailed in Nov. 2013.
Written Opinion (PCT/ISA/237) issued in PCT/JP2013/077682 mailed in Nov. 2013.
International Preliminary Report on Patentability (PCT/IPEA/409) issued in PCT/JP2013/077682 mailed in Sep. 2014.
ZHU et al., "Direct Asymmetric Vinylogous Aldol Reaction of Allyl Ketones with Isatins: Divergent synthesis of 3-Hydroxy-2-Oxindole Derivatives", Angewandte Chemie International Edition, vol. 52, No. 26, Jun. 24, 2013, pp. 6666-6670, XP055241010, DE, ISSN: 1443-7851, DOI: 10.1002/anie.201302274.
European Search Report dated Jan. 28, 2016, in a counterpart European patent application No. 13846040.7.

* cited by examiner

*Primary Examiner* — Michael Barker
(74) *Attorney, Agent, or Firm* — Chen Yoshimura LLP

(57) ABSTRACT

Disclosed is a compound of formula I: wherein $R^1$?, $R^2$?, $R^3$?, $R^4$?, $R^5$?, n and m are defined herein. The compound of formula I is prepared by a concise, catalytic enantioselective formal hetero-Diels-Alder (hDA) reactions of enones with isatins and is useful for making pharmaceutical composition for the treatment of proliferative diseases.

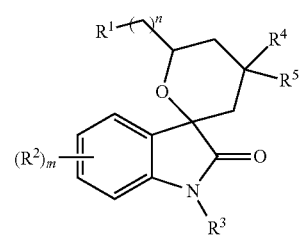

14 Claims, No Drawings

SPIROOXINDOLE DERIVATIVE AND PROCESS FOR PRODUCING THE SAME

TECHNICAL FIELD

The present invention relates to novel spirooxindole derivatives, their synthetic process, pharmaceutical compositions containing them and their use as therapeutic active substances.

BACKGROUND ART

Spirooxindole frameworks are common in bioactive natural products and pharmaceutical leads. The spirooxindole alkaloids such as mitraphylline, pteropodine, speciophylline and uncarine F are a class of natural products containing a priviledged bicyclic architecture. The development of efficient synthetic strategies to access spirooxindole motifs has been a challenge. The demand for concise asymmetric methods that provide a set of highly enantiomerically enriched spirooxindoles is high. Although syntheses of many types of spirooxindoles, including spirooxindole-derived cyclohexanones and lactols, have been reported, there are groups of spirooxindole motifs of interest that have not been efficiently and/or enantioselectively synthesized. The spirooxindole tetrahydropyranones (see Non-Patent Literature 1) are one such group. Tetrahydropyranones are important core structures and they can be transformed to substituted tetrahydropyrans and related derivatives, spirooxindole tetrahydropyranones should also be useful for further diversification.

Formal hetero-Diels-Alder (hDA) reactions, including highly enantioselective versions, are common routes to tetrahydropyranones. Most of the reported hDA reactions that afford tetrahydropyranones, however, use silyl enol ether-derived dienes or siloxybutadiene derivatives as dienes whether the catalysts are metal catalysts (see Non-Patent Literature 2) or hydrogen bonding-providing catalysts (see Non-Patent Literature 3).

PRIOR ART LITERATURES

Non-Patent Documents

[Non-Patent Literature 1] J. Wang, E. A. Crane, K. A. Scheidt, Org. Lett. 2011, 13, 3086-3089.

[Non-Patent Literature 2] M. Anada, T. Washio, N. Shimada, S. Kitagaki, M. Nakajima, M. Shiro, S. Hashimoto, Angew. Chem. 2004, 116, 2719-2722

[Non-Patent Literature 3] N. Momiyama, H. Tabuse, M. Terada, J. Am. Chem. Soc. 2009, 131, 12882-12883

SUMMARY OF THE INVENTION

The present inventors reasoned that enamine activation of enones in situ should provide concise, atom economical routes to tetrahydropyranones, and have found that concise, catalytic enantioselective formal hetero-Diels-Alder (hDA) reactions of enones with isatins that afford spirooxindole tetrahydropyranones. These findings have led to the present invention.

In one aspect, the present invention relates to novel compounds of formula I:

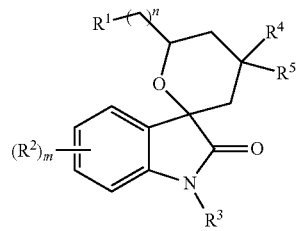

wherein
$R^1$ is hydrogen, halogen;
lower alkyl, lower cycloalkyl, lower alkenyl, lower alkynyl, lower alkoxy wherein these substituents are optionally substituted with halogen;
cyano, nitro; hydroxyl optionally protected with an appropriate protective group; amino optionally protected with an appropriate protective group,
aryl, heteroaryl wherein these substituents are optionally substituted with
halogen;
lower alkyl, lower alkoxy wherein these substituents are optionally substituted with halogen; or
cyano;
—C(=O)OR$^a$, —C(=O)NR$^a$R$^b$, —OC(=O)R$^a$, —OC(=O)OR$^a$, —OC(=O)NR$^a$R$^b$, —NHC(=O)NR$^a$R$^b$, —N{C(=O)R$^a$} {C(=O)R$^6$};
$R^a$ and $R^b$ are each independently hydrogen, hydroxyl; lower alkyl, lower cycloalkyl, lower alkenyl, lower alkynyl wherein these substituents are optionally substituted with halogen;
$R^a$ and $R^b$ together form —(CH$_2$)$_l$—, or
$R^a$ and $R^b$ taken together with the nitrogen atom to which they are attached, form heteroaryl
$R^2$ is, each independently, hydrogen, halogen; lower alkyl, lower alkoxy wherein these substituents are optionally substituted with halogen,
$R^3$ is hydrogen; lower alkyl, lower cycloalkyl wherein these substituents are optionally substituted with halogen or oxo;
lower alkyl-sulfonyl, aryl-sulfonyl; N-protecting group;
aryl, heteroaryl wherein these substituents are optionally substituted with alkyl, alkoxy, halogen, or hydroxyl;
$R^4$ and $R^5$ are each independently hydrogen, lower alkyl, lower alkenyl, lower alkynyl, lower alkoxy, hydroxyl optionally protected with an appropriate protective group, or amino optionally protected with an appropriate protective group, —NR$^a$R$^b$,
$R^4$ and $R^5$ taken together with the carbon atom to which they are attached, form carbonyl (C=O), oxime (C=NOR$^c$), hydrazone (C=N—NR$^c$R$^d$), acetal (C(OR$^c$)OR$^d$),
$R^c$ and $R^d$, are each independently hydrogen, lower alkyl, lower alkenyl, lower alkynyl, N-protecting group, or O-protecting group;
n is 0 to 12,
m is 0 to 4,
l is 2 to 8
or racemate, enantiomer, diastereomer, mixture thereof, or pharmaceutically acceptable salt thereof.

DETAILED DESCRIPTION OF THE INVENTION

In another aspect, the present invention relates to a process for the manufacture of compounds of formula I and intermediates or pharmaceutical compositions thereof. The present invention also relates to medicaments containing the said compounds or their pharmaceutically acceptable salts, to the use of the said compounds or their pharmaceutically acceptable salts for the treatment or prophylaxis of illnesses, especially in the treatment or prophylaxis of proliferative diseases.

The term "halogen" and "halo" are used interchangeably herein and denote fluoro, chloro, bromo, or iodo. Particular halogens are chloro and fluoro.

The term "lower alkyl" denotes a monovalent linear or branched saturated hydrocarbon group of 1 to 12 carbon atoms, in particular of 1 to 7 carbon atoms, more particular of 1 to 4 carbon atoms, for example, methyl, ethyl, n-propyl, isopropyl, n-butyl, iso-butyl, sec-butyl, and tert-butyl. Particular alkyl groups include methyl, ethyl, n-propyl and iso-propyl. More particular alkyl group is methyl.

The term "lower cycloalkyl", alone or in combination with other groups, denotes a monovalent saturated monocyclic or bicyclic hydrocarbon group of 3 to 10 ring carbon atoms, particularly a monovalent saturated monocyclic hydrocarbon group of 3 to 8 ring carbon atoms. Particular cycloalkyl groups are monocyclic. Examples for monocyclic cycloalkyl are cyclopropyl, cyclobutanyl, cyclopentyl, cyclohexyl or cycloheptyl.

The term "lower alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include methoxy, ethoxy, n-propoxy and isopropoxy.

The term "halo-alkyl" denotes an alkyl group wherein at least one of the hydrogen atoms of the alkyl group has been replaced by same or different halogen atoms. Examples of haloalkyl include fluoromethyl, difluoromethyl, trifluoromethyl, trifluoroethyl, trifluoromethylethyl and pentafluoroethyl. Particular haloalkyl group is trifluoromethyl.

The term "halo-alkoxy" denotes an alkoxy group wherein at least one of the hydrogen atoms of the alkoxy group has been replaced by same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups are trifluoromethoxy and trifluoroethoxy.

The term "alkenyl", alone or in combination, signifies an alkyl group of 2 to 12 carbon atoms, in particular of 2 to 7 carbon atoms, more particular of 2 to 4 as defined above, wherein one or more carbon-carbon single bond is replaced by a carbon-carbon double bond. Examples of alkenyl are ethenyl, n-propenyl, isopropenyl, n-butenyl or isobutenyl. Preferred alkenyl are ethenyl and n-propenyl.

The term "alkynyl", alone or in combination, signifies an alkyl group of 2 to 12 carbon atoms, in particular of 2 to 7 carbon atoms, more particular of 2 to 4 as defined above, wherein one or more carbon-carbon single bond is replaced by a carbon-carbon triple bond. Examples of alkynyl are ethynyl, n-propynyl, isopropynyl, n-butynyl or isobutynyl. Preferred alkenyl are ethynyl and n-propynyl.

The term "hydroxyl", alone or in combination with other groups, refers to —OH.

The term "oxo" denotes a divalent oxygen atom =O.

The term "oxo-lower-alkyl" denotes a lower alkyl wherein two geminal hydrogens atoms of the lower alkyl have been replaced by an oxo group. Particular example is 3-oxo-n-propyl, 3-oxo-n-butyl, 3-oxo-n-pentyl.

The term "oxo-lower-cycloalkyl" denotes a cycloalkyl wherein two geminal hydrogens atoms of the cycloalkyl have been replaced by an oxo group. Particular example is 3-oxo-cyclobutyl, 3-oxo-cyclopentyl, 3-oxo-cyclohexyl.

The term "cyano", alone or in combination with other groups, refers to —CN

The term "nitro", alone or in combination with other groups, refers to —NO$_2$.

The term "sulfonyl", alone or in combination with other groups, refers to —SO$_2$—.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups or hydroxy-protecting groups.

Particular amino-protecting groups are tert-butoxycarbonyl (Boc), benzyloxycarbonyl (Cbz), fluorenylmethoxycarbonyl (Fmoc) and benzyl (Bn).

Particular hydroxy-protecting groups are and methoxymethyl (MOM), 2-methoxyethoxymethyl (MEM), tetrahydropyranyl (THP), trimethylsilyl (TMS), tert-butyldimethylsilyl (TBS or TMDMS), tert-butyldimethylphenylsilyl (TBDPS), and benzyl (Bn).

The term "aryl", alone or in combination with other groups, refers to an aromatic carbocyclic group comprising 6 to 14, preferably 6 to 10, carbon atoms and having at least one aromatic ring or multiple condensed rings in which at least one ring is aromatic. Examples of "aryl" include benzyl, biphenyl, indanyl, naphthyl, phenyl (Ph) and the like. Preferred "aryl" is phenyl.

The term "heteroaryl", alone or in combination with other groups, refers to an aromatic carbocyclic group of having a single 4 to 8 membered ring or multiple condensed rings comprising 6 to 14, more preferably 6 to 10, ring atoms and containing 1, 2 or 3 heteroatoms individually selected from N, O and S, in particular N and O, in which group at least one heterocyclic ring is aromatic. Examples of "heteroaryl" include benzofuryl, benzoimidazolyl, benzooxazinyl, benzo thiazinyl, benzo thiazolyl, benzo thienyl, benzo triazolyl, furyl, imidazolyl, indazolyl, indolyl, isoquinolinyl, isothiazolyl, isoxazolyl, oxazolyl, pyrazinyl, pyrazolyl(pyrazyl), pyrazolo[1,5-a]pyridinyl, pyridazinyl, pyridinyl, pyrimidinyl, pyrrolyl, quinolinyl, tetrazolyl, thiazolyl, thienyl, triazolyl and the like. Preferred are 1H-pyrazolyl, furyl, isoxazolyl, oxazolyl, pyrazinyl, pyrazolyl, pyridazinyl, pyridinyl, pyridinyl-N-oxide and pyrimidinyl. More preferred heteroaryls are pyridinyl, pyrazolyl, pyrazinyl and pyrimidinyl. Most preferred are pyridin-2-yl, pyrazin-2-yl, 1H-pyrazol-3-yl and pyrimidin-2-yl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

An embodiment of the present invention is a compound of formula I:

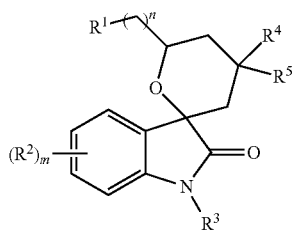

I wherein
$R^1$ is hydrogen, halogen;
lower alkyl, lower cycloalkyl, lower alkenyl, lower alkynyl, lower alkoxy wherein these substituents are optionally substituted with halogen;
cyano, nitro; hydroxyl optionally protected with an appropriate protective group; amino optionally protected with an appropriate protective group,
aryl, heteroaryl wherein these substituents are optionally substituted with
halogen;
lower alkyl, lower alkoxy wherein these substituents are optionally substituted with halogen; or
cyano;
—C(=O)$R^a$, —C(=O)N$R^aR^b$, —OC(=O)$R^a$, —OC(=O)O$R^a$, —OC(=O)N$R^aR^b$, —NHC(=O)N$R^aR^b$, —N{C(=O)$R^a$} {C(=O)$R^b$};
$R^a$ and $R^b$ are each independently hydrogen; lower alkyl, lower cycloalkyl, lower alkenyl, lower alkynyl wherein these substituents are optionally substituted with halogen;
$R^a$ and $R^b$ together form —(CH$_2$)$_l$—, or
$R^a$ and $R^b$ taken together with the nitrogen atom to which they are attached, form heteroaryl
$R^2$ is, each independently, hydrogen, halogen, hydroxyl; lower alkyl, lower alkoxy wherein these substituents are optionally substituted with halogen,
$R^3$ is hydrogen; lower alkyl, lower cycloalkyl wherein these substituents are optionally substituted with halogen or oxo;
lower alkyl-sulfonyl, aryl-sulfonyl; N-protecting group;
aryl, heteroaryl wherein these substituents are optionally substituted with alkyl, alkoxy, halogen, or hydroxyl;
$R^4$ and $R^5$ are each independently hydrogen, lower alkyl, lower alkenyl, lower alkynyl, lower alkoxy, hydroxyl optionally protected with an appropriate protective group, or amino optionally protected with an appropriate protective group, —N$R^aR^b$,
$R^4$ and $R^5$ taken together with the carbon atom to which they are attached, form carbonyl (C=O), oxime (C=NO$R^c$), hydrazone (C=N—NR$^c$R$^d$), acetal (C(OR$^c$)OR$^d$),
$R^c$ and $R^d$, are each independently hydrogen, lower alkyl, lower alkenyl, lower alkynyl, N-protecting group, or O-protecting group;
n is 0 to 12,
m is 0 to 4,
l is 2 to 8
or racemate, enantiomer, diastereomer, mixture thereof, or pharmaceutically acceptable salt thereof.

A further embodiment of the present invention is the compound of formula I as described herein,
wherein
$R^1$ is hydrogen, halogen;
lower alkyl, lower alkenyl, lower alkynyl, lower alkoxy wherein these substituents are optionally substituted with halogen;
cyano, nitro, hydroxyl optionally protected with an appropriate protective group, amino optionally protected with an appropriate protective group
aryl which is optionally substituted with
halogen;
lower alkyl, lower alkoxy wherein these substituents are optionally substituted with halogen or cyano;
—C(=O)O$R^a$, —C(=O)N$R^aR^b$, —N{C(=O)$R^a$} {C(=O)$R^b$};
$R^a$ and $R^b$ are each independently hydrogen; lower alkyl, lower cycloalkyl, lower alkenyl, lower alkynyl wherein these substituents are optionally substituted with halogen;
$R^a$ and $R^b$ taken together with the nitrogen atom to which they are attached, form heteroaryl
$R^2$ is, each independently, hydrogen, halogen, hydroxyl; lower alkyl, lower alkoxy wherein these substituents are optionally substituted with halogen,
$R^3$ is hydrogen; lower alkyl, lower cycloalkyl which is optionally substituted with halogen or oxo; lower alkyl-sulfonyl, aryl-sulfonyl; or N-protecting group;
$R^4$ and $R^5$ are each independently hydrogen, lower alkyl, lower alkenyl, lower alkynyl, hydroxyl optionally protected with an appropriate protective group, amino optionally protected with an appropriate protective group,
$R^4$ and $R^5$ taken together with the carbon atom to which they are attached, form carbonyl (C=O), oxime (C=NO$R^c$), hydrazone (C=N—NR$^c$R$^d$),
$R^c$ and $R^d$ are each independently hydrogen, lower alkyl, lower alkenyl, lower alkynyl, O-protecting group, N-protecting group;
n is 0 to 8,
m is 0 to 4,
l is 2 to 4
or racemate, enantiomer, diastereomer, mixture thereof, or pharmaceutically acceptable salt thereof.

Another further embodiment of the present invention is the compound of formula I as described herein,
wherein
$R^1$ is hydrogen, halogen;
lower alkyl, lower alkenyl, lower alkynyl, lower alkoxy wherein these substituents are optionally substituted with halogen;
hydroxyl optionally protected with an appropriate protective group, amino optionally protected with an appropriate protective group aryl which is optionally substituted with
halogen;
lower alkyl, lower alkoxy wherein these substituents are optionally substituted with halogen; or
cyano;
—C(=O)OR$^a$, —C(=O)NR$^a$R$^b$, —N{C(=O)R$^a$}{C(=O)R$^b$};

R$^a$ and R$^b$ are each independently hydrogen; lower alkyl, lower cycloalkyl, lower alkenyl, lower alkynyl wherein these substituents are optionally substituted with halogen;

R$^a$ and R$^b$ taken together with the nitrogen atom to which they are attached, form phthalimide R$^2$ is, each independently, hydrogen, halogen; lower alkyl, lower alkoxy wherein these substituents are optionally substituted with halogen, R$^3$ is hydrogen; lower alkyl, lower cycloalkyl which is optionally substituted with halogen or oxo; lower alkyl-sulfonyl, or aryl-sulfonyl;

R$^4$ and R$^5$ are each independently hydrogen, lower alkyl, lower alkenyl, lower alkynyl, hydroxyl, amino optionally protected with an appropriate protective group, R$^4$ and R$^5$ taken together with the carbon atom to which they are attached, form carbonyl (C=O), hydrazone (C=N—NR$^c$R$^d$), R$^c$ and R$^d$ is hydrogen and benzyl;

n is 0 to 6, m is 0 to 2 or racemate, enantiomer, diastereomer, mixture thereof, or pharmaceutically acceptable salt thereof.

A further embodiment of the present invention is the compound of formula I as described herein, wherein R$^1$ is chloro, fluoro, bromo, methyl, ethyl, n-propyl, isopropyl, ethenyl (vinyl), n-propenyl(allyl), isopropenyl, ethynyl, n-propynyl, isopropynyl, hydroxyl, methoxy, ethyoxy, n-propoxy, isopropoxy, tert-buthyldimethylsiliyloxy, phenyl, 4-methy-lphenyl, 4-methoxy-phenyl, 4-hydroxy-phenyl, 4-cyano-phenyl, or 1,3-dioxoisoindolin-2-yl.

A particular embodiment of the present invention is the compound of formula I as described herein, wherein R$^1$ is chloro, methyl, ethyl, isopropyl, ethenyl(vinyl), n-propenyl (allyl), isopropenyl, ethynyl, hydroxyl, tert-buthyldimethylsiliyloxy, phenyl, or 1,3-dioxoisoindolin-2-yl.

A further embodiment of the present invention is the compound of formula I as described herein, wherein R$^2$ is hydrogen, chloro, fluoro, bromo, methyl, ethyl, n-propyl, isopropyl, methoxy, ethyoxy, n-propoxy, isopropoxy.

A particular embodiment of the present invention is the compound of formula I as described herein, wherein R$^2$ is hydrogen, chloro, bromo, or methyl.

A further embodiment of the present invention is the compound of formula I as described herein, wherein R$^3$ is hydrogen, methyl, ethyl, n-propyl, isopropyl, cyclopropyl, cyclobutyl, cylcopentyl, cyclohexyl, phenyl, benzyl, 3-oxo-n-propyl, 3-oxo-n-butyl, 3-oxo-n-pentyl, 3-oxo-cyclobutyl, 3-oxo-cyclopentyl, 3-oxo-cyclohexyl, methylsulphonyl, ethylsulphonyl, n-propylsulphonyl, isopropylsulphonyl, phenylsulphonyl, 4-methyl-phenyl-suphonyl.

A further embodiment of the present invention is the compound of formula I as described herein, wherein R$^3$ is hydrogen, methyl, ethyl, n-propyl, isopropyl, cyclopropyl, cyclobutyl, cylcopentyl, cyclohexyl, phenyl, benzyl, 3-oxo-n-propyl, 3-oxo-n-butyl, 3-oxo-n-pentyl, 3-oxo-cyclobutyl, 3-oxo-cyclopentyl, 3-oxo-cyclohexyl, methylsulphonyl, ethylsulphonyl, n-propylsulphonyl, isopropylsulphonyl, phenylsulphonyl, 4-methyl-phenyl-suphonyl.

A particular embodiment of the present invention is the compound of formula I as described herein, wherein R$^3$ is hydrogen, methyl, benzyl, 3-oxo-n-butyl, 3-oxo-cyclohexyl, methylsulphonyl, phenylsulphonyl, 4-methyl-phenyl-suphonyl.

A further embodiment of the present invention is the compound of formula I as described herein, wherein R$^4$ and R$^5$ are each independently hydrogen, methyl, ethyl, n-propyl, isopropyl, ethenyl(vinyl), n-propenyl(allyl), isopropenyl, ethynyl, n-propynyl, isopropynyl, hydroxyl, methoxy, ethyoxy, n-propoxy, isopropoxy, amino, diemthylamino, benzylamino.

A particular embodiment of the present invention is the compound of formula I as described herein, wherein R$^4$ and R$^5$ are each independently hydrogen, methyl, n-propenyl (allyl), hydroxyl, methoxy, amino, benzylamino.

A further embodiment of the present invention is the compound of formula I as described herein, wherein R$^4$ and R$^5$ are taken together with the carbon atom to which they are attached, form C=O, C=NOH, C=N—NHBn.

A further embodiment of the present invention is the compound of formula I as described herein, wherein n is 0, 1, or 2.

A further embodiment of the present invention is the compound of formula I as described herein, wherein m is 0 or 1.

A particular embodiment of the compound of formula I as described herein, selected from the group consisting of:

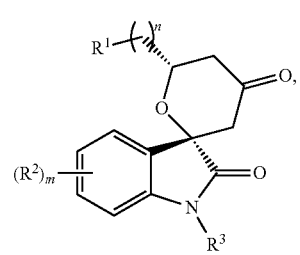

II-1

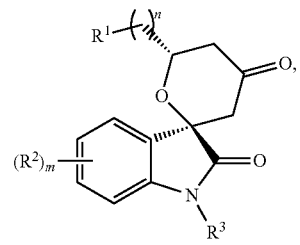

II-2

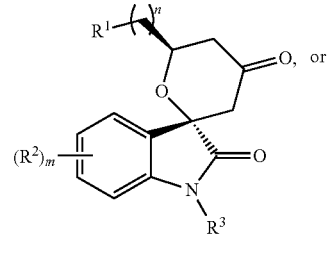

II-3

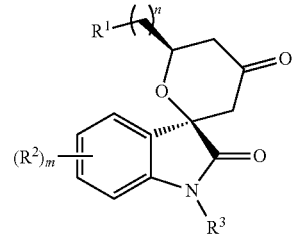

II-4 and pharmaceutically acceptable salts thereof.

Particular examples of a compound of formula I as described herein, selected from the group consisting of: (2'S,6'R)-6'-Propyl-5',6'-dihydrospiro[indoline-3,2'-pyran)-2,4'(3'H)-dione, (2'S,6'S)-6'-Propyl-5',6'-dihydrospiro[indoline-3,2'-pyran)-2,4'(3'H)-dione, (2'R,6'S)-6'-Propyl-5',6'-dihydrospiro[indoline-3,2'-pyran)-2,4'(3'H)-dione, (2'R,6'R)-6'-Propyl-5',6'-dihydrospiro[indoline-3,2'-pyran)-2,4'(3'H)-dione, (2'S,6'R)-4-chloro-6'-propyl-5',6'-dihydrospiro[indoline-3,2'-pyran]-2,4'(3'H)-dione, (2'S,6'S)-4-chloro-6'-propyl-5',6'-dihydrospiro[indoline-3,2'-pyran]-2,4'(3'H)-dione, (2'R,6'S)-4-chloro-6'-propyl-5',6'-dihydrospiro[indoline-3,2'-pyran]-2,4'(3'H)-dione, (2'R,6'R)-4-chloro-6'-propyl-5',6'-dihydrospiro[indoline-3,2'-pyran]-2,4'(3'H)-dione, (2'S,6'R)-4-bromo-6'-propyl-5',6'-dihydrospiro[indoline-3,2'-pyran]-2,4'(3'H)-dione, (2'S,6'S)-4-bromo-6'-propyl-5',6'-dihydrospiro[indoline-3,2'-pyran]-2,4'(3'H)-dione, (2'R,6'S)-4-bromo-6'-propyl-5',6'-dihydrospiro[indoline-3,2'-pyran]-2,4'(3'H)-dione, (2'R,6'R)-4-bromo-6'-propyl-5',6'-dihydrospiro[indoline-3,2'-pyran]-2,4'(3'H)-dione, (2'S,6'R)-5-methyl-6'-propyl-5',6'-dihydrospiro[indoline-3,2'-pyran]-2,4'(3'H)-dione, (2'S,6'S)-5-methyl-6'-propyl-5',6'-dihydrospiro[indoline-3,2'-pyran]-2,4'(3'H)-dione, (2'R,6'S)-5-methyl-6'-propyl-5',6'-dihydrospiro[indoline-3,2'-pyran]-2,4'(3'H)-dione, (2'R,6'R)-5-methyl-6'-propyl-5',6'-dihydrospiro[indoline-3,2'-pyran]-2,4'(3'H)-dione, (2'S,6'R)-5-bromo-6'-propyl-5',6'-dihydrospiro[indoline-3,2'-pyran]-2,4'(3'H)-dione, (2'S,6'S)-5-bromo-6'-propyl-5',6'-dihydrospiro[indoline-3,2'-pyran]-2,4'(3'H)-dione, (2'R,6'S)-5-bromo-6'-propyl-5',6'-dihydrospiro[indoline-3,2'-pyran]-2,4'(3'H)-dione, (2'R,6'R)-5-bromo-6'-propyl-5',6'-dihydrospiro[indoline-3,2'-pyran]-2,4'(3'H)-dione, (2'S,6'R)-6-chloro-6'-propyl-5',6'-dihydrospiro[indoline-3,2'-pyran]-2,4'(3'H)-dione, (2'S,6'S)-6-chloro-6'-propyl-5',6'-dihydrospiro[indoline-3,2'-pyran]-2,4'(3'H)-dione, (2'R,6'S)-6-chloro-6'-propyl-5',6'-dihydrospiro[indoline-3,2'-pyran]-2,4'(3'H)-dione, (2'R,6'R)-6-chloro-6'-propyl-5',6'-dihydrospiro[indoline-3,2'-pyran]-2,4'(3'H)-dione, (2'S,6'R)-6'-hexyl-5',6'-dihydrospiro[indoline-3,2'-pyran]-2,4'(3'H)-dione, (2'S,6'S)-6'-hexyl-5',6'-dihydrospiro[indoline-3,2'-pyran]-2,4'(3'H)-dione, (2'R,6'S)-6'-hexyl-5',6'-dihydrospiro[indoline-3,2'-pyran]-2,4'(3'H)-dione, (2'R,6'R)-6'-hexyl-5',6'-dihydrospiro[indoline-3,2'-pyran]-2,4'(3'H)-dione, (2'S,6'S)-6'-isopropyl-5',6'-dihydrospiro[indoline-3,2'-pyran]-2,4'(3'H)-dione, (2'S,6'R)-6'-isopropyl-5',6'-dihydrospiro[indoline-3,2'-pyran]-2,4'(3'H)-dione, (2'R,6'R)-6'-isopropyl-5',6'-dihydrospiro[indoline-3,2'-pyran]-2,4'(3'H)-dione, (2'R,6'S)-6'-isopropyl-5',6'-dihydrospiro[indoline-3,2'-pyran]-2,4'(3'H)-dione, (2'S,6'R)-6'-phenethyl-5',6'-dihydrospiro[indoline-3,2'-pyran]-2,4'(3'H)-dione, (2'S,6'S)-6'-phenethyl-5',6'-dihydrospiro[indoline-3,2'-pyran]-2,4'(3'H)-dione, (2'R,6'S)-6'-phenethyl-5',6'-dihydrospiro[indoline-3,2'-pyran]-2,4'(3'H)-dione, (2'R,6'R)-6'-phenethyl-5',6'-dihydrospiro[indoline-3,2'-pyran]-2,4'(3'H)-dione, (2'S,6'R)-6'-(but-3-yn-1-yl)-5',6'-dihydrospiro[indoline-3,2'-pyran]-2,4'(3'H)-dione, (2'S,6'S)-6'-(but-3-yn-1-yl)-5',6'-dihydrospiro[indoline-3,2'-pyran]-2,4'(3'H)-dione, (2'R,6'S)-6'-(but-3-yn-1-yl)-5',6'-dihydrospiro[indoline-3,2'-pyran]-2,4'(3'H)-dione, (2'R,6'R)-6'-(but-3-yn-1-yl)-5',6'-dihydrospiro[indoline-3,2'-pyran]-2,4'(3'H)-dione, (2'S,6'R)-6'-(but-3-en-1-yl)-5',6'-dihydrospiro[indoline-3,2'-pyran]-2,4'(3'H)-dione, (2'S,6'S)-6'-(but-3-en-1-yl)-5',6'-dihydrospiro[indoline-3,2'-pyran]-2,4'(3'H)-dione, (2'R,6'S)-6'-(but-3-en-1-yl)-5',6'-dihydrospiro[indoline-3,2'-pyran]-2,4'(3'H)-dione, (2'R,6'R)-6'-(but-3-en-1-yl)-5',6'-dihydrospiro[indoline-3,2'-pyran]-2,4'(3'H)-dione, (2'S,6'R)-6'-(2-(1,3-dioxoisoindolin-2-yl)ethyl)-5',6'-dihydrospiro[indoline-3,2'-pyran]-2,4'(3'H)-dione, (2'S,6'S)-6'-(2-(1,3-dioxoisoindolin-2-yl)ethyl)-5',6'-dihydrospiro[indoline-3,2'-pyran]-2,4'(3'H)-dione, (2'R,6'S)-6'-(2-(1,3-dioxoisoindolin-2-yl)ethyl)-5',6'-dihydrospiro[indoline-3,2'-pyran]-2,4'(3'H)-dione, (2'R,6'R)-6'-(2-(1,3-dioxoisoindolin-2-yl)ethyl)-5',6'-dihydrospiro[indoline-3,2'-pyran]-2,4'(3'H)-dione, (2'S,6'R)-6'-(3-((tert-butyldimethylsilyl)oxy)propyl)-5',6'-dihydrospiro[indoline-3,2'-pyran]-2,4'(3'H)-dione, (2'S,6'S)-6'-(3-((tert-butyldimethylsilyl)oxy)propyl)-5',6'-dihydrospiro[indoline-3,2'-pyran]-2,4'(3'H)-dione, (2'R,6'S)-6'-(3-((tert-butyldimethylsilyl)oxy)propyl)-5',6'-dihydrospiro[indoline-3,2'-pyran]-2,4'(3'H)-dione, (2'R,6'R)-6'-(3-((tert-butyldimethylsilyl)oxy)propyl)-5',6'-dihydrospiro[indoline-3,2'-pyran]-2,4'(3'H)-dione, (2'S,6'R)-6'-(3-chloropropyl)-5',6'-dihydrospiro[indoline-3,2'-pyran]-2,4'(3'H)-dione, (2'S,6'S)-6'-(3-chloropropyl)-5',6'-dihydrospiro[indoline-3,2'-pyran]-2,4'(3'H)-dione, (2'R,6'S)-6'-(3-chloropropyl)-5',6'-dihydrospiro[indoline-3,2'-pyran]-2,4'(3'H)-dione, (2'R,6'R)-6'-(3-chloropropyl)-5',6'-dihydrospiro[indoline-3,2'-pyran]-2,4'(3'H)-dione, (2'R,6'R)-6'-phenyl-5',6'-dihydrospiro[indoline-3,2'-pyran]-2,4'(3'H)-dione, (2'R,6'S)-6'-phenyl-5',6'-dihydrospiro[indoline-3,2'-pyran]-2,4'(3'H)-dione, (2'S,6'S)-6'-phenyl-5',6'-dihydrospiro[indoline-3,2'-pyran]-2,4'(3'H)-dione, (2'S,6'R)-6'-phenyl-5',6'-dihydrospiro[indoline-3,2'-pyran]-2,4'(3'H)-dione, (2'S,4'R,6'R)-4'-hydroxy-6'-propyl-3',4',5',6'-tetrahydrospiro[indoline-3,2'-pyran]-2-one, (2'S,4'R,6'S)-4'-hydroxy-6'-propyl-3',4',5',6'-tetrahydrospiro[indoline-3,2'-pyran]-2-one, (2'S,4'S,6'R)-4'-hydroxy-6'-propyl-3',4',5',6'-tetrahydrospiro[indoline-3,2'-pyran]-2-one, (2'R,4'R,6'R)-4'-hydroxy-6'-propyl-3',4',5',6'-tetrahydrospiro[indoline-3,2'-pyran]-2-one, (2'R,4'S,6'S)-4'-hydroxy-6'-propyl-3',4',5',6'-tetrahydrospiro[indoline-3,2'-pyran]-2-one, (2'R,4'S,6'R)-4'-hydroxy-6'-propyl-3',4',5',6'-tetrahydrospiro[indoline-3,2'-pyran]-2-one, (2'R,4'R,6'S)-4'-hydroxy-6'-propyl-3',4',5',6'-tetrahydrospiro[indoline-3,2'-pyran]-2-one, (2'S,4'S,6'S)-4'-hydroxy-6'-propyl-3',4',5',6'-tetrahydrospiro[indoline-3,2'-pyran]-2-one, (2'S,4'R,6'R)-4'-(benzylamino)-6'-propyl-3',4',5',6'-tetrahydrospiro[indoline-3,2'-pyran]-2-one, (2'S,4'R,6'S)-4'-(benzylamino)-6'-propyl-3',4',5',6'-tetrahydrospiro[indoline-3,2'-pyran]-2-one, (2'S,4'S,6'R)-4'-(benzylamino)-6'-propyl-3',4',5',6'-tetrahydrospiro[indoline-3,2'-pyran]-2-one, (2'R,4'R,6'l?)-4'-(benzylamino)-6'-propyl-3',4',5',6'-tetrahydrospiro[indoline-3,2'-pyran]-2-one, (2'R,4'S,6'S)-4'-(benzylamino)-6'-propyl-3',4',5',6'-tetrahydrospiro[indoline-3,2'-pyran]-2-one, (2'R,4'S,6'R)-4'-(benzylamino)-6'-propyl-3',4',5',6'-tetrahydrospiro[indoline-3,2'-pyran]-2-one, (2'R,4'R,6'S)-4'-(benzylamino)-6'-propyl-3',4',5',6'-tetrahydrospiro[indoline-3,2'-pyran]-2-one, (2'S,4'S,6'S)-4'-(benzylamino)-6'-propyl-3',4',5',6'-tetrahydrospiro[indoline-3,2'-pyran]-2-one, (2'S,4'R,6'R)-4'-allyl-4'-hydroxy-6'-propyl-3',4',5',6'-tetrahydrospiro[indoline-3,2'-pyran]-2-one, (2'S,4'R,6'S)-4'-allyl-4'-hydroxy-6'-propyl-3',4',5',6'-tetrahydrospiro[indoline-3,2'-pyran]-2-one, (2'S,4'S,6'R)-4'-allyl-4'-hydroxy-6'-propyl-3',4',5',6'-tetrahydrospiro[indoline-3,2'-pyran]-2-one, (2'R,4'R,6'R)-4'-allyl-4'-hydroxy-6'-propyl-3',4',5',6'-tetrahydrospiro[indoline-3,2'-pyran]-2-one, (2'R,4'S,6'S)-4'-allyl-4'-hydroxy-6'-propyl-3',4',5',6'-tetrahydrospiro[indoline-3,2'-pyran]-2-one, (2'R,4'S,6'R)-4'-allyl-4'-hydroxy-6'-propyl-3',4',5',6'-tetrahydrospiro[indoline-3,2'-pyran]-2-one, (2'R,4'R,6'S)-4'-allyl-4'-hydroxy-6'-propyl-3',4',5',6'-tetrahydrospiro[indoline-3,2'-pyran]-2-one, (2'S,4'S,6'S)-4'-allyl-4'-hydroxy-6'-propyl-3',4',5',6'-tetrahydrospiro[indoline-3,2'-pyran]-2-one, 4-Methyl-N'-((2'S,6'R)-2-oxo-6'-propyl-5',6'-dihydrospiro[indoline-3,2'-pyran]-4'(3'H)-ylidene)benzenesulfonohydrazide, 4-Methyl-N'-((2'S,6'S)-2-oxo-6'-propyl-5',6'-dihydrospiro[indoline-3,2'-pyran]-4'(3'H)-ylidene)benzenesulfonohydrazide, 4-Methyl-N'-((2'R,6'S)-2-oxo-6'-propyl-5',6'-dihydrospiro[indoline-3,2'-pyran]-4'(3'H)-ylidene)benzenesulfonohydrazide, and 4-Methyl-N'-((2'R,6'R)-2-oxo-6'-propyl-5',6'-dihydrospiro[indoline-3,2'-pyran]-4'(3'H)-ylidene)benzenesulfonohydrazide, or pharmaceutically acceptable salts thereof.

Processes for the manufacture of compounds of formula (I) as described herein are an object of the invention.

Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein.

General Procedure of Preparation of Compound of Formula I

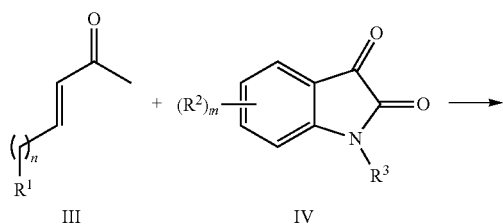

Compound of formula I can be prepared by hetero Diels-Alder reaction of compound of formula II (enones) and compound of formula IV (isatins) to form compound of formula II, followed by transformation of carbonyl group, wherein $R^1$, $R^2$, $R^3$, $R^4$, and $R^5$ are defined above (Scheme 1).

General Procedure of Preparation of Compound of Formula III (enones)

Compound of formula III can be prepared by oxidation of alcohol, wherein $R^1$ is defined above, followed by reaction with 1-(triphenylphosphoranylidene)-2-propanone according to methods know in the art (Scheme 2). Oxidation of alcohol is achieved by oxidant such as PDC, PCC, and PCC/celite in the solvent such as $CH_2Cl_2$ and $CHCl_3$. In case $R^1$ is N-protecting group or O-protecting group, the protecting group can be cleaved according to methods know in the art. In case $R^1$ is hydroxyl group, $R^1$ can be modified to obtain ester, carbonate, or carbamate derivatives according to methods know in the art. In case $R^1$ is amino group, $R^1$ can be modified to obtain amide or urea derivatives according to methods know in the art.

General Procedure of Preparation of Compound of Formula IV (isatins)

Compound of formula IV is commercially available or can be prepared by oxidatinon of compound of formula IV' (indole derivatives), wherein $R^2$ and $R^3$ are defined above according to methods know in the art such as by use of PCC in 1,2-dicloroethane, at rt to reflux described in Synlett, (13), 2013-2027; 2008 (Scheme 3-1).

General Procedure of Preparation of Compound of Formula IV''' (isatins)

Compound of formula IV''' is commercially available or can be prepared by reaction of compound of formula IV'''' (aniline derivatives) with 2,2,2-trichloroethane-1,1-diol wherein $R^2$ and $R^3$ are defined above according to methods know in the art such as by use of HCl, $H_2NOH$, and $Na_2SO_4$ in $H_2O$ at rt to 80° C. described in Journal of Medicinal Chemistry, 48(8), 3045-3050; 2005: Journal of Medicinal Chemistry, 50(1), 40-64; 2007, etc. (Scheme 3-2).

General Procedure of Preparation of Compound of Formula IV (isatins)

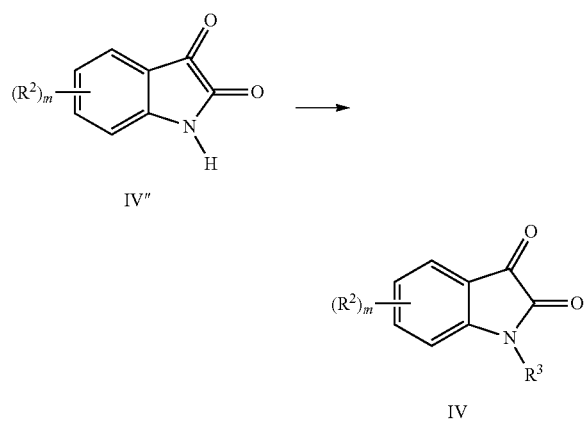

Compound of formula IV is commercially available or can be prepared by introduction of $R^3$ group on indole nitrogen of compound of formula IV‴, wherein $R^2$ and $R^3$ are defined above according to methods know in the art (Scheme 4).

Introduction of $R^3$ group on indole nitrogen can be achieved by nuclephilic substitution by use of $R^3$—X ($R^3$ is, for example, alkyl, halo-alkyl, halo-cycloalkyl, alkenyl, halo-alkeynl, alkynyl, halo-alkynyl, N-protecting group such as benzyl, 4-methoxybenzyl, MOM (methoxy-methyl-), phenyl, acetyl, N,N-dimethylaminosulfonyl, mesithylenesulfonyl, p-methoxyphenylsulfonyl, benzensulfonyl, toluensulfonamide and the like; X is chloro, bromo, or iodo), optionally in the presence of base such as NaH, NaOH, Et$_3$N, DBU, imidazole and the like, in the solvent such as CH$_2$Cl$_2$ and DMSO. Introduction of $R^3$ group on indole nitrogen can be achieved by 1,4-addition by use of α,β-unsaturated ketones such as methyl vinyl ketone and 2-cyclohexen-1-one, optionally in the presence of base such as DBU, or triphenylphosphine (PPh$_3$) and the like, in the solvent such as CH$_2$Cl$_2$ and DMSO. Alternatively, introduction of $R^3$ group on indole nitrogen can be achieved by carbamation by use of (Boc)$_2$O, TrocCl, TeocCl and the like, optionally in the presence of base such as NaH, NaOH, Et$_3$N, DBU and the like, in the solvent such as CH$_2$Cl$_2$ and DMSO.

General Procedure of Preparation of Compound of Formula II (spirooxindole tetrahydropyranones) by Hetero-Diels-Alder Reactions

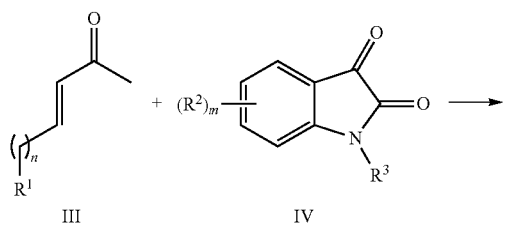

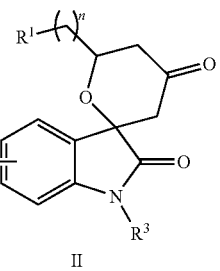

Compound of formula II can be prepared by Hetero Diels-Alder reaction of Enone II and Isatin IV, wherein $R^1$, $R^2$ and $R^3$ are defined above (Scheme 5).

General Procedure of Preparation of Compound of Formula II' (spirooxindole tetrahydropyranones) by Hetero-Diels-Alder Reactions

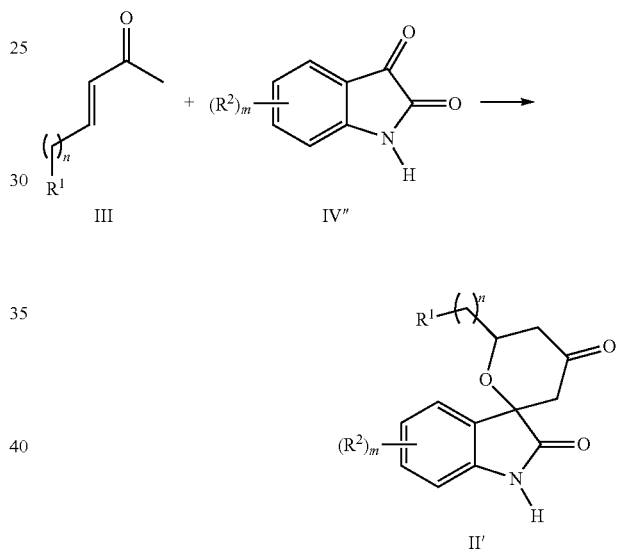

Compound of formula II' can be prepared by Hetero Diels-Alder reaction of Enone II and Isatin IV', wherein $R^1$ and $R^2$ are defined above (Scheme 6). An embodiment of the present inventon is a process for preparing a compound of formula II:

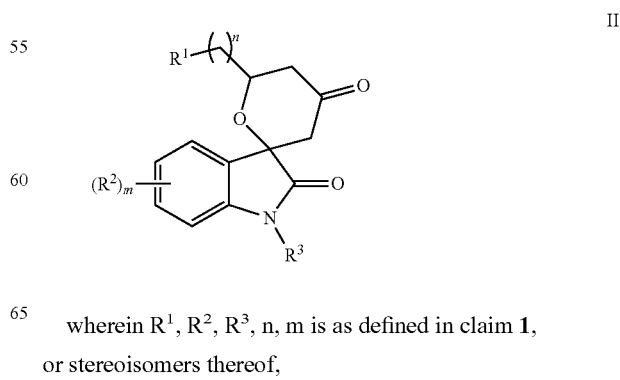

wherein $R^1$, $R^2$, $R^3$, n, m is as defined in claim 1, or stereoisomers thereof, which process comprises reacting a compound of formula III:

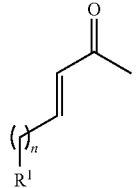
III wherein R¹ is as defined in the above;
with a compound of formula IV:

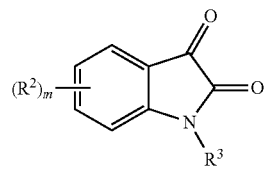
IV wherein R², R³, m are as defined in the above;

in the presence of at least one amine selected from the group consisting of the following compounds represented by formulae A, B, C, D, E, F, G, H, and stereoisomers thereof and in the presence of at least one acid selected from the group consisting of the following compounds represented by formulae I, J, K, L, M, N, and stereoisomers thereof, and with or without additive O or molecular sieves 4A

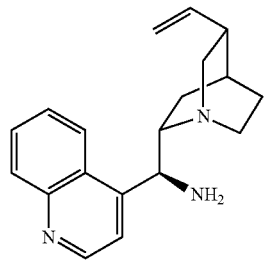
A

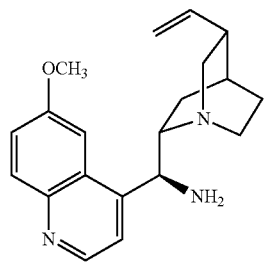
B

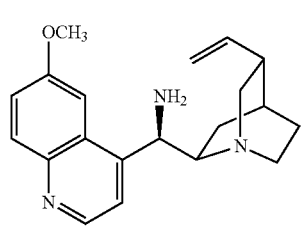
C

-continued

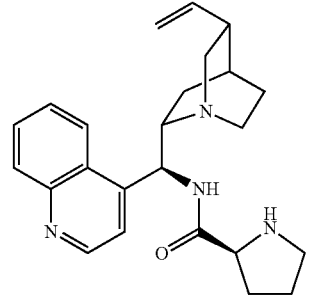
D

E

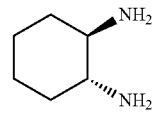
F

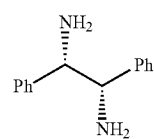
G

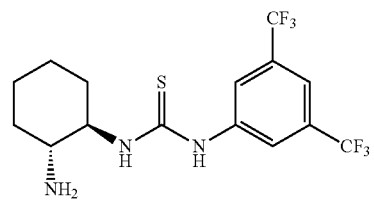
H

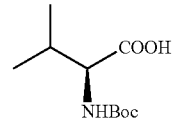
I

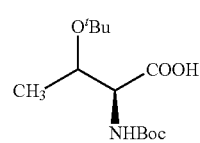
J

CH₃COOH
K

CF₃COOH
L

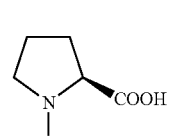
M

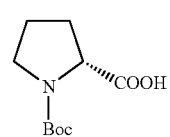
N

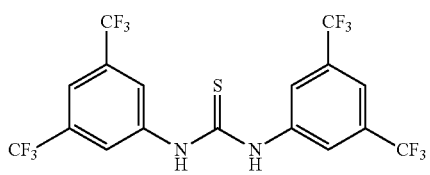

(S)-quinolin-4-yl((1S,2S,4S,5R)-5-vinylquinuclidin-2-yl)methanamine (Amine A)
(S)-(6-methoxyquinolin-4-yl)((1S,2S,4S,5R)-5-vinylquinuclidin-2-yl)methanamine (Amine B)
(R)-(6-methoxyquinolin-4-yl)((1S,2S,4S,5R)-5-vinylquinuclidin-2-yl)methanamine (Amine C)
(S)—N—((S)-quinolin-4-yl((1S,2S,4S,5R)-5-vinylquinuclidin-2-yl)methyl)pyrrolidine-2-carboxamide (Amine D)
(R)-2-amino-4-methylpentan-1-ol (Amine E)
(1S,2S)-cyclohexane-1,2-diamine (Amine F)
(1S,2S)-1,2-diphenylethane-1,2-di amine (Amine G)
1-((1S,2S)-2-aminocyclohexyl)-3-(3,5-bis(trifluoromethyl)phenyl)thiourea (Amine H)
(S)-2-((tert-butoxycarbonyl)amino)-3-methylbutanoic acid (Acid I)
(2S,3R)-3-(tert-butoxy)-2-((tert-butoxycarbonyl)amino)butanoic acid (Acid J)
acetic acid (Acid K)
2,2,2-trifluoroacetic acid (Acid L)
(S)-1-(tert-butoxycarbonyl)pyrrolidine-2-carboxylic acid (Acid M)
(R)-1-(tert-butoxycarbonyl)pyrrolidine-2-carboxylic acid (Acid N)
1,3-bis(3,5-bis(trifluoromethyl)phenyl)thiourea (Thiourea O)

In a preferred embodiment of the present invention, a process for preparing a compound of formula II':

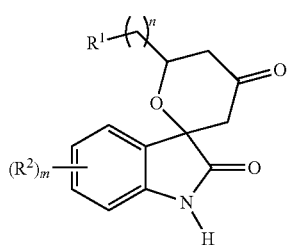

II' wherein $R^1$, $R^2$, $R^3$, n, m is as defined in claim 1,
or stereoisomers thereof,
which process comprises reacting a compound of formula III:

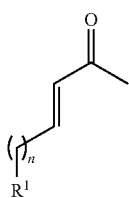

III wherein $R^1$ is as defined in the above;

with a compound of formula IV":

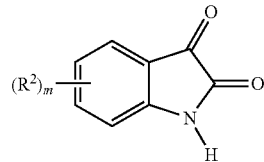

IV"

wherein $R^2$, m are as defined in the above;
in the presence of at least one amine selected from the group consisting of the following compounds represented by formulae A, B, C, D, E, F, G, H, and stereoisomers thereof and in the presence of at least one acid selected from the group consisting of the following compounds represented by formulae I, J, K, L, M, N, and stereoisomers thereof, and with or without additive O or molecular sieves 4A In a preferred embodiment of the present invention, the amine is A or F.

In a preferred embodiment of the present invention, the acid is I or J.

In a preferred embodiment of the present invention, the additive is O.

In a further preferred embodiment of the present invention, $R^1$ is lower alkyl, the amine is A, acid is J, and the additive is O.

In a further preferred embodiment of the present invention, $R^1$ is aryl, n=0, the amine is F, and acid is I or J.

In a further preferred embodiment of the present invention, a compound of formula II is a compound of formula

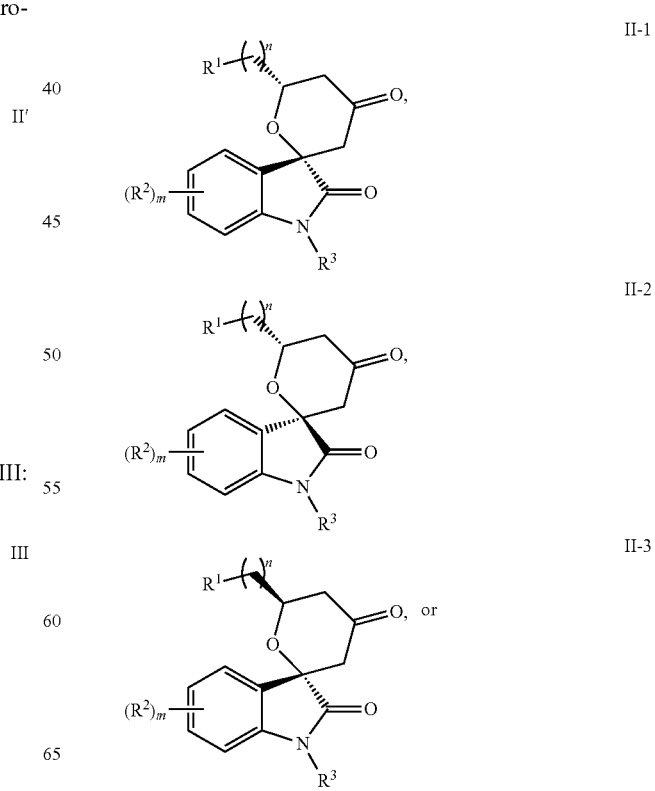

-continued

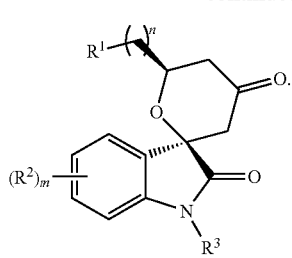

II-4

In a further preferred embodiment of the present invention, spirooxindole derivatives of formula I is spirooxindole derivatives of compound II-1.

In a preferred embodiment of the present invention, the molar ratio of the unsaturated ketones to the amine is 1:0.02 to 0.2

In a further preferred embodiment of the present invention, the molar ratio of the unsaturated ketones to the additive is 1:0.02 to 0.2

In a preferred embodiment of the present invention, the reaction is carried out in a solvent.

In a further preferred embodiment of the present invention, the solvent is selected from aromatic hydrocarbons, in particular toluene, trimethylbenzene or trifluoromethylbenzene.

General Procedure of Preparation of Compound of Formula II (spirooxiindole tetrahydropyranones)

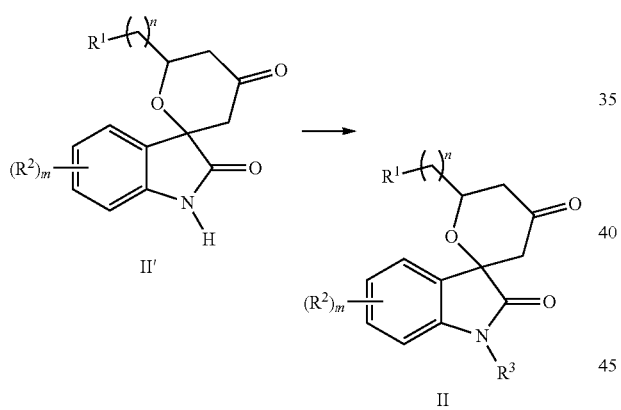

Compound of formula II can be prepared by introduction of $R^3$ group on indole nitrogen of compound of formula II', wherein $R^1$, $R^2$, and $R^3$ are defined above according to methods know in the art such as analogy to Scheme 4 (Scheme 7).

General Procedure of Preparation of Compound of Formula I

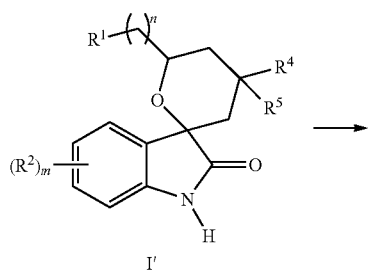

-continued

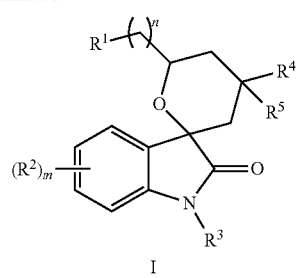

I

Compound of formula I can be prepared by introduction of $R^3$ group on indole nitrogen of compound of formula I', wherein $R^1$, $R^2$, and $R^3$ are defined above according to methods know in the art such as analogy to Scheme 4 (Scheme 8).

General Procedure of Reduction of Carbonyl Moiety of Compound of Formula I-a

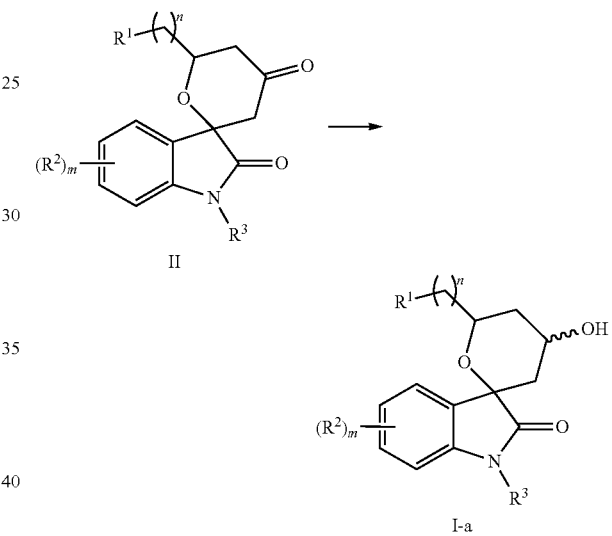

Compound of formula I-a can be prepared by reduction of carbonyl moiety of compound of formula II, wherein $R^1$, $R^2$, and $R^3$ are defined above according to methods know in the art (Scheme 9). Reduction of carbonyl moiety of compound of formula II can be achieved by use of reductant such as $NaBH_4$, $NaBH_3CN$, and $NaBH(OAc)_3$, etc. in the solvent such as MeOH, $CH_2Cl_2$, and THF, etc at 0° C. to room temperature.

General Procedure of Reductive Amination of Carbonyl Moiety of Compound of Formula I-b

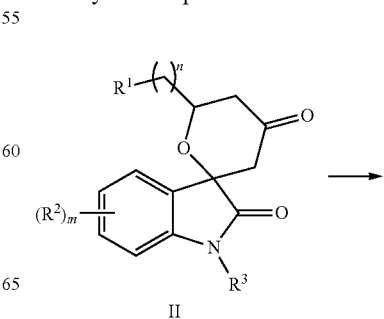

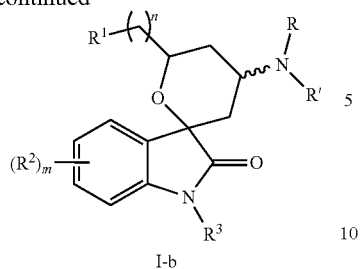

I-b

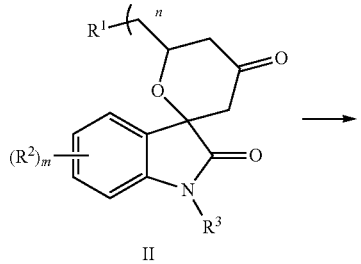

II

Compound of formula I-b can be prepared by reductive amination of carbonyl moiety of compound of formula II, wherein $R^1$, $R^2$, and $R^3$ are defined above, and R and R' are each independently hydrogen, lower alkyl, lower cycloalkyl, lower alkenyl, lower alkynl, phenyl, benzyl, or tolyl optionally substituted by halogen; or R and R' taken together with nitrogen atom to which they are attached to form cyclic amine according to methods know in the art (Scheme 10). Reductive amination of carbonyl moiety of compound of formula II can be achieved by use of reductant such as $NaBH_4$, $NaBH_3CN$, and $NaBH(OAc)_3$, etc., amine (RR'NH) such as methyl amine, dimethyl amine, cyclopropyl amine, pheyl amine, benzyl amine, piperidine, and piperazine, etc., in the solvent such as $CH_2Cl_2$ and THF etc., at 0° C. to room temperature.

General Procedure of Nucleophilic Addition of Carbonyl Moiety of Compound of Formula I-c

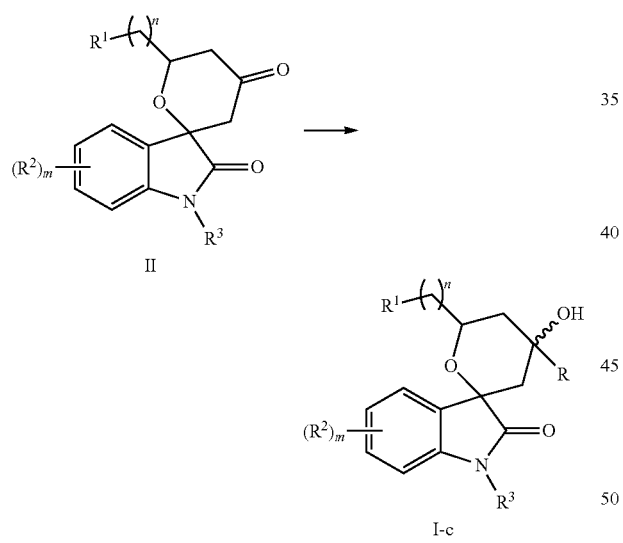

Compound of formula I-c can be prepared by nucleophilic addition of carbonyl moiety of compound of formula II, wherein $R^1$, $R^2$, and $R^3$ are defined above, and R is lower alkyl, lower cycloalkyl, lower alkenyl, lower alkynl, phenyl, or benzyl, optionally substituted by halogen according to methods know in the art (Scheme 11). Nucleophilic addition of carbonyl moiety of compound of formula II can be achieved by use of nucleophilic reagent such as RLi, RMgBr, and R2CuLi, or metal such as Li Mg, Cu, In and alkyl halide (RX) such as methyl bromide, allyl bromide, benzyl bromide, etc. in the solvent such as $CH_2Cl_2$, DMF, and THF etc., at −78° C. to room temperature.

General Procedure of Hydrazination of Carbonyl Moiety of Compound of Formula I-d Compound of formula I-d can be prepared by oximation of carbonyl moiety of compound of formula II, wherein $R^1$, $R^2$, and $R^3$ are defined above, and R and R' are each independently hydrogen, lower alkyl, lower cycloalkyl, lower alkenyl, lower alkynl, phenyl, benzyl, optionally substituted by halogen or lower alkyl sulfonyl, aryl sulfonyl; or R and R' taken together with nitrogen atom to which they are attached to form heteroaryl according to methods know in the art (Scheme 12). Hydrazination of carbonyl moiety of compound of formula II can be achieved by use of hydrazine derivative ($H_2N$—NRR') such as methyl hydrazine, dimethyl hydrazine, phenyl hydrazine, benzyl hydrazine, piperidine hydrazine, p-tosyl hydrazine, and 1-phthalazinylhydrazine etc. in the solvent such as $CH_2Cl_2$ and THF etc., at 0° C. to room temperature.

General Procedure of Oximation of Carbonyl Moiety of Compound of Formula I-e

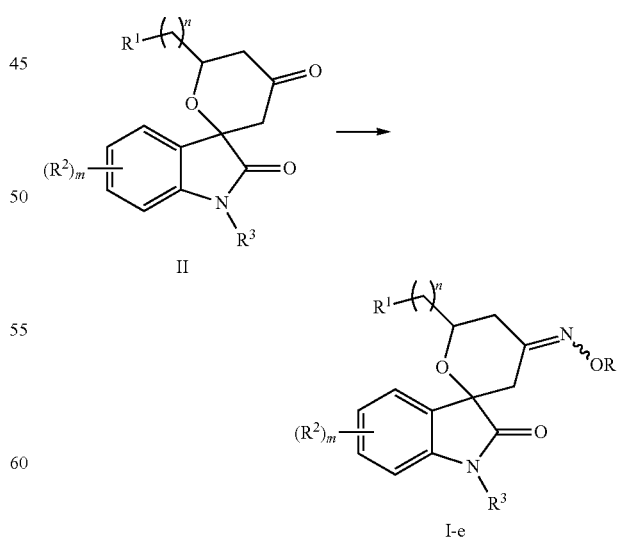

Compound of formula I-e can be prepared by oximation of carbonyl moiety of compound of formula II, wherein $R^1$, $R^2$, and $R^3$ are defined above, and R is hydrogen, lower alkyl, lower cycloalkyl, lower alkenyl, lower alkynl, phenyl, benzyl, or tolyl optionally substituted by halogen according to methods know in the art (Scheme 13). Oximation of carbonyl moiety of compound of formula II can be achieved by use of alkoxy amine derivative (H$_2$N—OR') such as methoxy amine, phenyl amine, and benzyloxy amine, etc. in the solvent such as CH$_2$Cl$_2$ and THF etc., at 0° C. to room temperature.

General Procedure of Acetalization of Carbonyl Moiety of Compound of Formula I-f

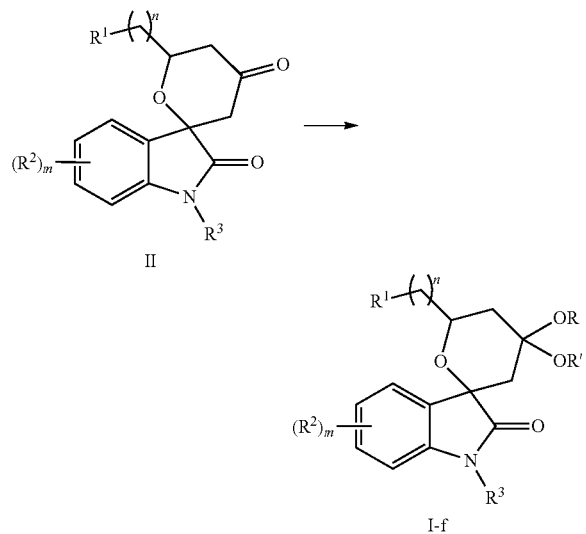

Compound of formula I-f can be prepared by acetalization of carbonyl moiety of compound of formula II, wherein R$^1$, R$^2$, and R$^3$ are defined above, and R and R' are lower alkyl, benzyl, or R and R' together form —(CH$_2$)$_n$— (n=2 or 3), according to methods know in the art (Scheme 14). Acetalization of carbonyl moiety of compound of formula II can be achieved by use of alcohol such as methanol, ethanol, and benzyl alcohol etc. in the presence of acid such as HCl, TsOH, and TFA etc., in the solvent such as CH$_2$Cl$_2$, THF, and acetone etc., at 0° C. to room temperature.

Also an object of the present invention is a compound according to fomula I as described herein for use as therapeutically active substance.

In a preferred embodiment of the present invention is a compound according to fomula I as described herein for use as therapeutically active substance for the treatment or prophylaxis of proliferative diseases.

In a preferred embodiment of the present invention is a compound according to fomula I as described herein for use as therapeutically active substance for the treatment or prophylaxis of cancers.

Likewise an object of the present invention is a pharmaceutical composition comprising a compound according to fomula I as described herein and a pharmaceutically acceptable adjuvant.

A particular embodiment of the present inventon is the pharmaceutical composition as described herein for the treatment or prophylaxis of proliferative diseases.

A particular embodiment of the present inventon is the pharmaceutical composition as described herein for the treatment or prophylaxis of cancers.

Also an object of the present invention is the use of a compound according to fomula I as described herein for the preparation of a medicament for the treatment or prophylaxis of proliferative diseases.

Also an object of the present invention is the use of a compound according to fomula I as described herein for the preparation of a medicament for the treatment or prophylaxis of cancers.

Pharmacological Tests

The compound of formula I and their pharmaceutically acceptable salts possess valuable pharmacological properties. It has been found that the compounds of the present invention are associated with anti-cancer activity, endocrine/cardiovascular activity, and function in bone formation. The compounds were investigated in accordance with the test given hereinafter.

Cytotoxicity:

K562 cells (American Type Culture Collection) were cultured in a culture medium containing 10% (v/v) fetal calf serum (FCS) (manufactures by Sigma) to logarithmic phase. The cells were seeded in 96-well microtiter plate at a density of 5000 cells/well in 100 μL cell culture medium and incubated at 37° C. and 5% CO$_2$ in a humidified incubator overnight. The test compounds of various concentrations were added in a well at 10 fold concentration in ¹/₁₀ volume of medium without FCS. After 6-48 hrs incubation at 37° C. in the CO$_2$ incubator, 10 μL solution of the viable cell counting reagent, Cell counting Kit-8 (5 mmol/L WST-8, 0.2 mmol/L 1-Methoxy PMS, 150 mmol/L NaCl) (manufactured by Dojindo) was added to each well, and reacted for 1 to 4 hours in the CO$_2$ incubator. After the incubation, an absorbance of formazan, generated by reduction of WST-8 was determined at 450 nm using a microplate reader.

The assay readout is correlated with the viable cell numbers. Small values correspond to high inhibition and larger values to low inhibition of the cell growth. To determine IC$_{50}$ values (i.e. the concentration inhibiting the cell growth by 50%) of the compound of formula I, several assays were made with a range of concentrations chosen empirically to give low, high and intermediate inhibition of the growth and determined using the curve fitting software.

The exemplified compounds according to formula I have an inhibitory activity in this assays (IC$_{50}$) particular less than 1000 μM, more particular less than 100 μM. IC$_{50}$ values can be converted logarithmically to pIC$_{50}$ values (−log IC$_{50}$), in which higher values indicate exponentially greater potency. The IC$_{50}$ value is not an absolute value but depends on experimental conditions e.g. concentrations employed.

Hexokinase 2 Inhibition

It is well known that tumor cells mainly rely on glycolysis for energy generation and intermediary metabolism, a phenomenon known as the Warburg effect. Hexokinase-II (HK-II), a key enzyme of glycolysis, catalyzes the first step in the conversion of glucose to glucose-6-phosphate. HK-II is highly expressed in many types of tumors and its expression is correlated with glucose uptake, tumor aggressiveness, and poor survival prognosis. Inhibition of HK-II activity attenuates tumor cell growth and induces apoptosis.

The test compounds were added to a typical reaction mixture of HK-II, and the produced ADP concentrations were determined using Transcreener® ADP$^2$ FI Assay (BellBrook Labs, Madison, Wis., USA).

The results are shown in Table 1.

TABLE 1

| Example No. | Compound No. | Structure | HK-II Inhibition ADP-FP (% inhibition at 20 μM) | Cytotoxicity K562 IC$_{50}$ (μM) |
|---|---|---|---|---|
| 11 | 3aa | 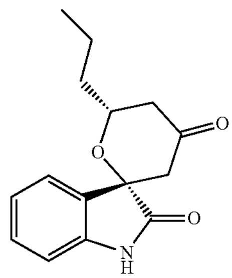 [SMILES: CCC[C@@H]1CC(=O)C[C@@]2(O1)C(=O)Nc1ccccc12] | not tested | 125 μM (99% ee: 130 μM) |
| 26 | 5 | 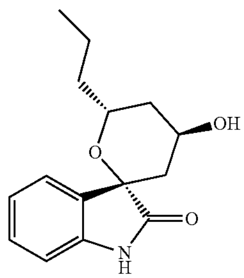 [SMILES: CCC[C@@H]1C[C@@H](O)C[C@@]2(O1)C(=O)Nc1ccccc12] | not tested | >245 μM (92% ee: >245 μM) |
| 28 | 7 | 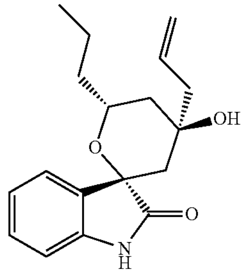 [SMILES: C=CC[C@@]1(O)C[C@@H](CCC)O[C@]2(C1)C(=O)Nc1ccccc12] | not tested | >212 μM (87% ee: >212 μM) |
| 22 | 3ga | 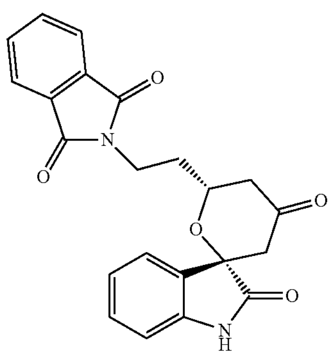 [SMILES: O=C1C[C@@H](CCN2C(=O)c3ccccc3C2=O)O[C@]2(C1)C(=O)Nc1ccccc12] | not tested | 91% ee: 113 μM |
| 13 | 3ac | 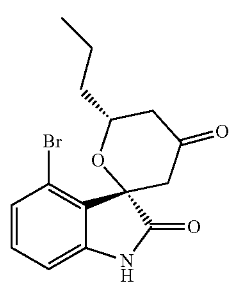 [SMILES: CCC[C@@H]1CC(=O)C[C@@]2(O1)C(=O)Nc1cccc(Br)c12] | not tested | 82% ee: 16 μM |

TABLE 1-continued

| Example No. | Compound No. | Structure | HK-II Inhibition ADP-FP (% inhibition at 20 μM) | Cytotoxicity K562 IC$_{50}$ (μM) |
|---|---|---|---|---|
| 12 | 3ab | 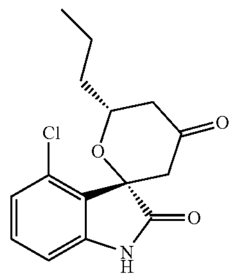 [SMILES: CCC[C@@H]1CC(=O)C[C@@]2(O1)C(=O)Nc1cccc(Cl)c12] | not tested | 15 μM |
| 15 | 3ae | 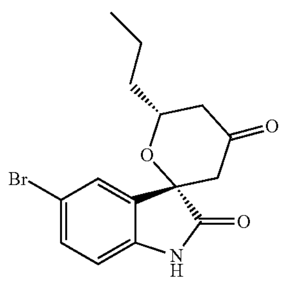 [SMILES: CCC[C@@H]1CC(=O)C[C@@]2(O1)C(=O)Nc1ccc(Br)cc12] | not tested | 20 μM |
| 16 | 3af | 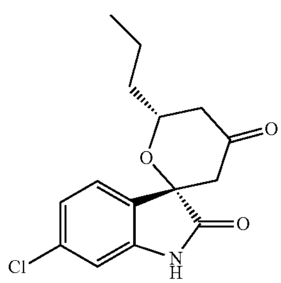 [SMILES: CCC[C@@H]1CC(=O)C[C@@]2(O1)C(=O)Nc1cc(Cl)ccc12] | not tested | 21 μM |
| 14 | 3ad | 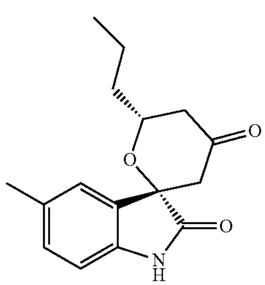 [SMILES: CCC[C@@H]1CC(=O)C[C@@]2(O1)C(=O)Nc1ccc(C)cc12] | not tested | not tested |
| 27 | 6 | 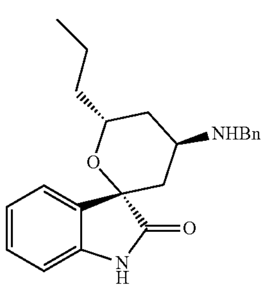 | 37.7% | not tested |

| Example No. | Compound No. | Structure | HK-II Inhibition ADP-FP (% inhibition at 20 μM) | Cytotoxicity K562 IC$_{50}$ (μM) |
|---|---|---|---|---|
| 25 | 3ja | 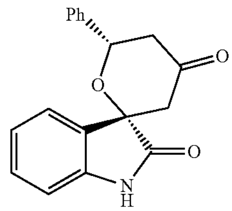 [SMILES: O=C1C[C@@H](c2ccccc2)O[C@]2(C1)C(=O)Nc1ccccc12] | 33.8% | not tested |

In addition, some of the above compounds, such as compound Nos. 3ac, 3ab, 3ae, 3af and 3ja showed an activity selectively lethal to tumor cells in which both WNT and KRas signaling pathways are activated.

Pharmaceutical Compositions

The compound of formula I as well as their pharmaceutical acceptable salts can be used as medicaments, e.g. in the form of pharmaceutical preparations. The pharmaceutical preparations can be administered orally, e.g. in the form of tablets, coated tablets, dragees, hard and soft capsules, solutions, emulsions or suspensions. The administration can however, also be effected rectally, e.g. in the form of suppositories, or parenterally, e.g. in the form of injection solutions.

The compounds of formula I and their pharmaceutical acceptable salts can be processed with pharmaceutically inert, inorganic or organic excipients for the production of tablets, coated tablets, gragees and hard gelatine capsules. Lactose, corn starch or derivatives thereof, talc, stearic acid or its salts etc can be used as such excipients e.g. for tablets, dragees and hard gelatine capsules.

Suitable excipients for soft gelatine capsules are e.g. vegetable oils, waxes, fats, semisolid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can be vary within wide limits and will, of course, be fitted to the individual requirements in each particular case. In general, in the case of oral administration a daily dosage of about 10 to 1000 mg per person of a compound of general formula I should be appropriate, although the above upper limit can be exceeded when necessary.

The invention in illustrated hereinafter by Examples, which have no limiting character.

In case the preparative examples are obtained as a mixture of enantiomers and diastereomers, the pure enantiomers or diastereomers can be separated by methods described herein or by methods known to the person skilled in the art, such as e.g. chiral chromatography or crystallization.

1. Preparation of Enones (E)-hept-3-en-2-one (enone 1a)

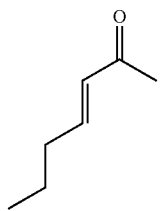

Enone 1a was purchased from Alfa Aesar and used without purification.

(E)-dec-3-en-2-one (enone 1b)

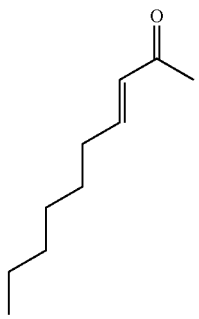

Enone 1b, and 1c was purchased from Wako Pure Chemical Industries and used without further purification.

(E)-5-methylhex-3-en-2-one (enone 1c)

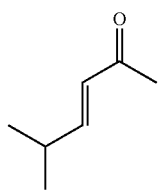

Enone 1c was purchased from Tokyo Chemical Industry and used without further purification.

(E)-6-phenylhex-3-en-2-one (enone 1d)

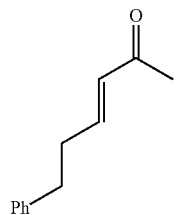

3-phenylpropan-1-al (5.0 mmol) was dissolved in CH$_2$Cl$_2$ (15 mL). To this solution, 1-(triphenylphosphoranylidene)-2-propanone (5.0 mmol) was added and the solution was refluxed for 24 h. The mixture was concentrated and purified by flash column chromatography (hexane/EtOAc) to give enone 1d. 63%; colorless oil.

(E)-oct-3-en-7-yn-2-one (enone 1e)

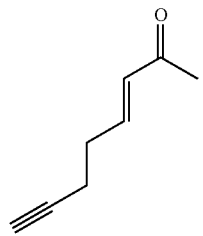

A mixture of pent-4-yn-1-ol (10 mmol), PCC (4.3 g, 20 mmol), and celite (4.3 g) in CH$_2$Cl$_2$ (30 mL) was stirred at room temperature for 1 h. The mixture was diluted with CH$_2$Cl$_2$, filtered, and concentrated. The resulting pale yellow oil was dissolved in CH$_2$Cl$_2$ (30 mL). To this solution, 1-(triphenylphosphoranylidene)-2-propanone (33 mmol) was added and the solution was refluxed for 24 h. The mixture was concentrated and purified by flash column chromatography (hexane/EtOAc) to give enone 1e. 30%; colorless oil. The spectroscopic data matched those reported previously in H. Wu, S. Radomkit, J. M. O'Brien, A. M.; Hoveyda, J. Am. Chem. Soc. 2012, 134, 8277.

(E)-oct-3,7-dien-2-one (enone 1f)

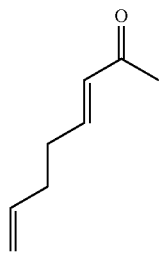

The title compound was prepared in analogy to enone 1e from pent-4-en-1-ol. 44%; colorless oil. $^1$H NMR (400 MHz, CDCl$_3$): δ 6.80 (m, 1H), 6.09 (m, 1H), 5.81 (m, 1H), 5.09-5.01 (m, 2H), 2.35-2.30 (m, 2H), 2.30-2.17 (m, 5H). $^{13}$C NMR (100 MHz, CDCl$_3$): δ 198.6, 147.4, 137.0, 131.6, 115.7, 32.1, 31.7, 26.9.

(E)-2-(5-oxohex-3-en-1-yl)isoindoline-1,3-dione (enone 1g)

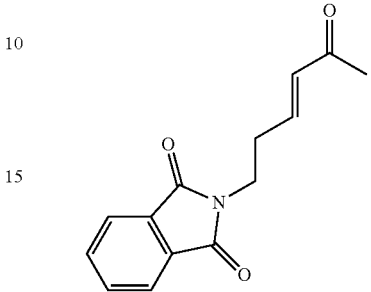

The title compound was prepared in analogy to enone 1e from 2-(3-hydroxypropyl)isoindoline-1,3-dione. 58%; colorless solid; mp: 93-95. $^1$H NMR (400 MHz, CDCl$_3$): δ 7.77-7.74 (m, 2H), 7.68-7.64 (m, 2H), 6.71 (dt, J=16.0 Hz, 7.2 Hz, 1H), 6.00 (d, J=16.0 Hz, 1H), 3.79 (t, J=7.2 Hz, 2H), 2.59-2.53 (m, 2H), 2.16 (s, 3H). $^{13}$C NMR (100 MHz, CDCl$_3$): δ 198.2, 168.1, 143.6, 134.1, 133.3, 131.8, 123.3, 36.3, 31.6, 26.7.

(E)-7-((tert-butyldimethylsilyl)oxy)hept-3-en-2-one (enone 1h)

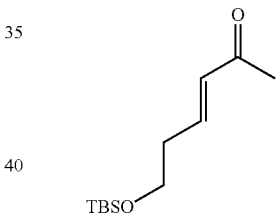

The title compound was prepared in analogy to enone 1e from 3-((tert-butyldimethylsilyl)oxy)propan-1-ol. 41%; colorless oil. $^1$H NMR (400 MHz, CDCl$_3$): δ 6.83 (dt, J=16.0 Hz, 7.2 Hz, 1H), 6.09 (dt, J=16.0 Hz, 1.6 Hz, 1H), 3.64 (t, J=6.4 Hz, 2H), 2.32-2.27 (m, 2H), 2.24 (s, 3H), 1.72-1.65 (m, 2H), 0.90 (s, 9H), 0.05 (s, 6H). $^{13}$C NMR (100 MHz, CDCl$_3$): δ 198.6, 148.2, 131.4, 62.2, 31.2, 29.0, 26.8, 25.9, 18.3, −5.34.

(E)-7-clorohept-3-en-2-one (enone 1i)

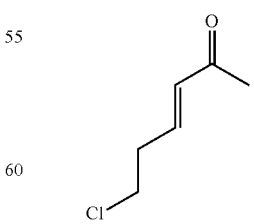

The title compound was prepared in analogy to enone 1e from 3-chloropropan-1-ol. 81%; colorless oil. $^1$H NMR (400 MHz, CDCl$_3$): δ 6.78 (dt, J=16.0 Hz, 6.8 Hz, 1H), 6.13 (dt, J=16.0 Hz, 1.2 Hz, 1H), 3.57 (t, J=6.4 Hz, 2H), 2.44-2.38 (m, 2H), 2.26 (s, 3H) 2.00-1.92 (m, 2H). $^{13}$C NMR (100 MHz, CDCl$_3$): 198.3, 146.0, 132.0, 44.0, 30.8, 29.5, 27.1.

(E)-4-phenylbut-3-en-2-one (enone 1j)

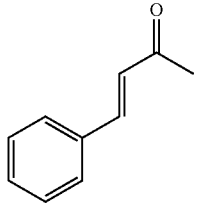

Enone 1j was purchased from Aldrich and used without further purification.

2. Preparation of Isatines

Indoline-2,3-dione (isatine 2a)

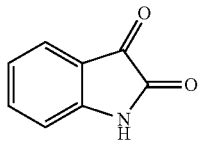 [SMILES: O=C1Nc2ccccc2C1=O]

Isatine 2a was purchased from Nacalai tesque and used without purification.

4-chloroindoline-2,3-dione (isatine 2b)

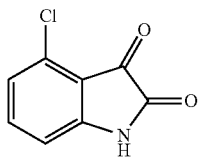 [SMILES: O=C1Nc2cccc(Cl)c2C1=O]

Isatine 2b was purchased from Tokyo Chemical Industry and used without purification.

4-bromoindoline-2,3-dione (isatine 2c)

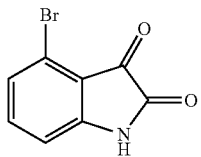 [SMILES: O=C1Nc2cccc(Br)c2C1=O]

Isatine 2c was purchased from Tokyo Chemical Industry and used without purification.

5-methylindoline-2,3-dione (isatine 2d)

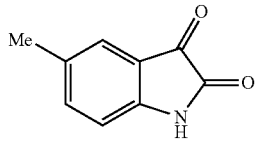 [SMILES: Cc1ccc2c(c1)C(=O)C(=O)N2]

Isatine 2d was purchased from Tokyo Chemical Industry and used without purification.

5-bromoindoline-2,3-dione (isatine 2e)

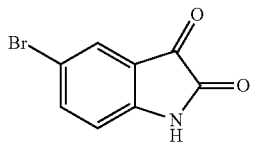 [SMILES: O=C1Nc2ccc(Br)cc2C1=O]

Isatine 2e was purchased from Tokyo Chemical Industry and used without purification.

6-chloroindoline-2,3-dione (isatine 2f)

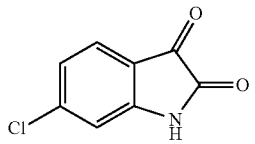 [SMILES: O=C1Nc2cc(Cl)ccc2C1=O]

Isatine 2f was purchased from Tokyo Chemical Industry and used without purification.

3. Preparation of Catalysts

Amine A

Amine A was synthesized by the reported procedure.

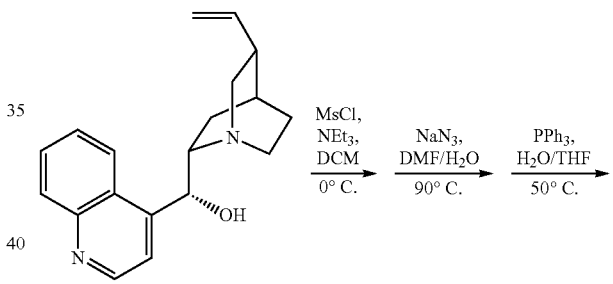

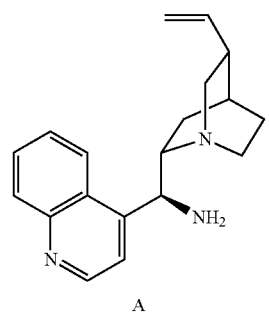

A

To a solution of cinchonidine (2.9 g, 10 mmol), triethylamine (4.2 mL, 30 mmol) in CH$_2$Cl$_2$ (200 mL) was added methanesulfonyl chloride (1.56 mL, 20 mmol) dropwise at 0° C. and the mixture was stirred at the same temperature. After 1 h, the mixture was washed with sat NaHCO$_3$ (100 mL×3) and brine (100 mL×2), dried over Na$_2$SO$_4$ and concentrated. The residue was dissolved in DMF/H$_2$O (5:1, 60 mL). To this solution was added NaN$_3$ (1.3 g, 20 mmol) and the resulting mixture was stirred at 90° C. for 4 h. After being cooled to room temperature, the mixture was poured into water and extracted with EtOAc (100 mL×3). Organic layers were combined, washed with water (100 mL×2) and brine (100 mL×2), dried over Na$_2$SO$_4$, and concentrated. The residue was purified by flash column chromatography (CH$_2$Cl$_2$/MeOH=40/1 to 20/1) to afford the corresponding azide derivative as a yellow oil (2.0 g, 63% yield). The azide derivative was dissolved in THF/H$_2$O (7:1, 70 mL) and triphenylphosphine (2.0 g, 6.3 mmol) was added. The mixture was stirred at 50° C. for 22 h. After being cooled to room temperature, the mixture was concentrated and extracted with aqueous HCl (1 N, 10 mL×2). Aqueous layers were combined, washed with CH$_2$Cl$_2$ (10 mL×3), made alkaline with saturated K$_2$CO$_3$, and extracted with CH$_2$Cl$_2$ (100 mL×3). Organic layers were combined, washed with brine (100 mL×2), dried over Na$_2$SO$_4$, concentrated. The residue was purified by flash column chromatography (CH$_2$Cl$_2$/MeOH=20/1 to CH$_2$Cl$_2$/MeOH/triethylamine=10/1/1) to afford amine A as a pale yellow viscous oil (1.23 g, 67%). $^1$H NMR (400 MHz, CDCl$_3$): δ 8.88 (d, J=4.4 Hz, 1H), 8.34 (brs, 1H), 8.20 (d, J=8.4 Hz, 1H), 7.69 (m, 1H), 7.57 (m, 1H), 7.50 (brd, J=4.4 Hz, 1H), 5.78 (ddd, J=17.2 Hz, 10.0 Hz, 7.6 Hz, 1H), 5.00-4.93 (m, 2H), 4.69 (brd, J=8.0 Hz, 1H), 3.28-3.14 (m, 2H), 3.05 (br, 1H), 2.82-2.73 (m, 2H), 2.27-2.24 (m, 1H), 1.97 (brs, 2H), 1.59-1.51 (m, 3H), 1.42-1.37 (m, 1H), 0.75-0.69 (m, 1H). $^{13}$C NMR (100 MHz, CDCl$_3$): δ 150.4, 148.6, 148.5, 141.9, 130.54, 130.47, 129.0, 127.7, 126.5, 123.3, 119.6, 114.3, 62.0, 56.3, 41.0, 39.9, 28.1, 27.6, 26.0. ESI-HRMS: calcd for C$_{19}$H$_{24}$N$_3$ (MH$^+$) 294.1970, found 294.1967.

Amines B, C, D, and H

Amines B and C were synthesized from the corresponding cinchona alkaloid alcohols by the procedure used for the synthesis of amine A. Amine D was synthesized from amine A and by the reported procedure. Amine H was synthesized by the reported procedure.

Amines E, F, and G

Amines E, F, and G were each purchased from Tokyo Chemical Industry, Wako Pure Chemical Industries, and Aldrich, and used without purification.

Acids I to N

Acids I to N were purchased from Wako Pure Chemical Industries and used without purification.

Thiourea O

Thiourea O was purchased from Tokyo Chemical Industry and used without purification.

4. Preparation of Spirooxindole Tetrahedropyranones and their Derivatives

Example 1

Product 3aa (2'S,6'R)-6'-Propyl-5',6'-dihydrospiro[indoline-3,2'-pyran]-2,4'(3'H)-dione (3aa Major Diastereomer)

To a solution of amine A (0.04 mmol, 11.8 mg) and acid J (0.08 mmol, 22.0 mg) in toluene (super dehydrated, 0.4 mL) were added thiourea O (0.04 mmol, 20.0 mg), enone 1a (1.0 mmol), and isatin 2a (0.2 mmol, 29.4 mg). The mixture (initially suspension) was stirred at room temperature (24° C.) until isatin was consumed (monitored by TLC). The mixture was purified by flash column chromatography (hexane/EtOAc=2:1 or hexane/acetone=3:1) to give product 3aa. The major diastereomer was separated from the minor diastereomer. The minor diastereomer (if existed) was obtained with the major diastereomer. The dr was determined by $^1$H NMR analysis before purification; the reaction mixture was diluted with CDCl$_3$ and this mixture was analyzed. Yield in Tables 2 and 3 was the yield of the major diastereomer of 3 (for dr>14:1 in the crude mixture) or of the combined yield of the major and minor diastereomers. The ee of the major diastereomer was determined by chiral-phase HPLC.

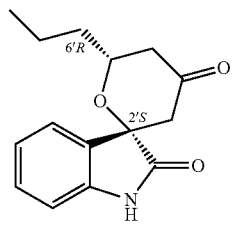 [SMILES: CCC[C@@H]1CC(=O)C[C@@]2(O1)C(=O)Nc1ccccc12]

Colorless crystals; mp 118-120° C. (from hexane/CH$_2$Cl$_2$, 99% ee). [α]$^{20}_D$ +126.1 (c 0.50, CH$_2$Cl$_2$, 99% ee). $^1$H NMR (400 MHz, CDCl$_3$): δ 8.65 (s, 1H), 7.31 (t, J=7.6 Hz, 1H), 7.18 (d, J=7.6 Hz, 1H), 7.02 (t, J=7.6 Hz, 1H), 6.96 (d, J=7.6 Hz, 1H), 4.33 (m, 1H), 3.09 (d, J=14.2 Hz, 1H), 2.66-2.61 (m, 2H), 2.42 (d, J=14.2 Hz, 1H), 1.75-1.70 (m, 1H), 1.58-1.53 (m, 1H), 1.41-1.26 (m, 2H), 0.84 (t, J=7.6 Hz, 3H). $^{13}$C NMR (100 MHz, CDCl$_3$): δ 205.5, 175.3, 140.5, 130.3, 128.3, 125.5, 122.8, 111.0, 78.8, 73.0, 47.7, 45.5, 38.3, 18.2, 13.7. ESI-HRMS: calcd for C$_{15}$H$_{17}$NO$_3$Na (MNa$^+$) 282.1106, found 282.1107. HPLC (Daicel Chiralpak IB, hexane/i-PrOH=90/10, flow rate 0.6 mL/min, λ=254 nm): t$_R$ (major diastereomer, major enantiomer, (2'S,6'R)-3aa)=18.9 min, t$_R$ (major diastereomer, minor enantiomer, (2'R,6'S)-3aa)=21.1 min, t$_R$ (mimor diastereomers (2'S*,6'S*)-3aa)=17.0 min and 18.0 min.

Product 3aa [(2'S,6'R)-3aa/(2'S*,6'S*)-3aa=1:1.4 $^1$H NMR (400 MHz, CDCl$_3$, * donates (2'S*,6'S*)-3aa): δ 8.65 (s, 1H×1/2.4), 8.31 (s, 1H*×1.4/2.4), 7.35-6.87 (m, 4H), 4.90 (m, 1H*×1.4/2.4), 4.33 (m, 1H×1/2.4), 3.09 (d, J=14.2 Hz, 1H×1/2.4), 2.77 (d, J=14.8 Hz, 1H*×1.4/2.4), 2.70-2.39 (m, 3H), 1.80-1.26 (m, 4H), 0.89 (t, J=7.2 Hz, 3H*×1.4/2.4), 0.84 (t, J=7.6 Hz, 3H×1/2.4). $^{13}$C NMR (100 MHz, CDCl$_3$, *donates (2'S*,6'S*)-3aa): δ 205.5, 204.7*, 176.8*, 175.3, 140.5, 140.3*, 130.3, 129.4*, 128.3, 125.5, 124.3*, 123.4*, 122.8, 111.0, 110.4*, 78.8, 78.0*, 73.0, 71.6*, 47.4, 46.9*, 45.6*, 45.5, 38.6*, 38.3, 18.2, 18.1*, 13.9*, 13.7.

Product (2'S*,6'S*)-3aa (minor diastereomer). (signals used for the determination of dr): $^1$H NMR (400 MHz, CDCl$_3$): δ 4.90 (m, 1H, CH$_2$CHO).

Example 2

Product 3ab (2'S,6'R)-4-chloro-6'-propyl-5',6'-dihydrospiro[indoline-3,2'-pyran]-2,4'(3'H)-dione (3ab Major Diastereomer)

The title compound was prepared in analogy to Example 1 from enone 1a, and isatin 2b by use of amine A, acid J, and thiourea O.

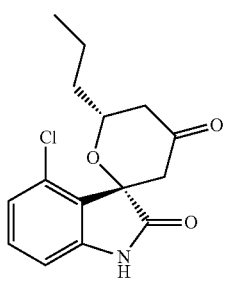 [SMILES: CCC[C@@H]1CC(=O)C[C@@]2(O1)C(=O)Nc1cccc(Cl)c12]

Pale yellow gum. [α]$^{20}_D$ −68.2 (c 1.05, CH$_2$Cl$_2$, 81% ee). $^1$H NMR (400 MHz, CDCl$_3$): δ 9.04 (s, 1H), 7.22 (t, J=8.0 Hz, 1H), 7.03 (d, J=8.0 Hz, 1H), 6.82 (d, J=8.0 Hz, 1H), 4.68 (m, 1H), 3.53 (d, J=16.8 Hz, 1H), 2.84 (dd, J=18.0 Hz, 12.0 Hz, 1H), 2.58 (dd, J=18.0 Hz, 2.0 Hz, 1H), 2.43 (d, J=16.8 Hz, 1H), 1.72-1.63 (m, 1H), 1.58-1.34 (m, 3H), 0.92 (t, J=7.6 Hz, 3H). $^{13}$C NMR (100 MHz, CDCl$_3$): δ 206.1, 177.9, 142.3, 131.4, 126.5, 124.2, 109.6, 78.6, 72.5, 46.0, 40.8, 18.3, 13.9. ESI-HRMS: calcd for C$_{15}$H$_{16}$ClNO$_3$Na (MNa$^+$) 316.0716, found 316.0717. HPLC (Daicel Chiralpak IB, hexane/i-PrOH=90/10, 0.6 mL/min, λ=254 nm): t$_R$ (major diastereomer, major enantiomer, (2'S,6'R)-3ab)=22.0 min, t$_R$ (major diastereomer, minor enantiomer, (2'R,6'S)-3ab)=25.6 min.

Example 3

Product 3ac (2'S,6'R)-4-bromo-6'-propyl-5',6-dihydrospiro[indoline-3,2'-pyran]-2,4'(3'H)-dione (3ac Major Diastereomer)

The title compound was prepared in analogy to Example 1 from enone 1 a, and isatin 2c by use of amine A, acid J, and thiourea O.

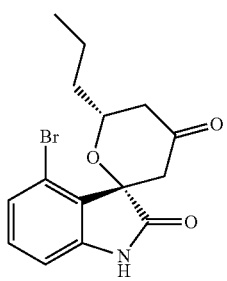 [SMILES: CCC[C@@H]1CC(=O)C[C@@]2(O1)C(=O)Nc1cccc(Br)c12]

Pale yellow amorphous solid. [α]$^{20}_D$ −84.7 (c 1.24, CH$_2$Cl$_2$, 82% ee). $^1$H NMR (400 MHz, CDCl$_3$): δ 8.26 (s, 1H), 7.22 (d, J=7.6 Hz, 1H), 7.14 (t, J=7.6 Hz, 1H), 6.82 (d, J=7.6 Hz, 1H), 4.78-4.73 (m, 1H), 3.66 (d, J=16.8 Hz, 1H), 2.97 (dd, J=18.4 Hz, 12.4 Hz, 1H), 2.56 (dd, J=18.4 Hz, 2.0 Hz, 1H), 2.36 (d, J=16.8 Hz, 1H), 1.71-1.41 (m, 4H), 0.94 (t, J=7.2 Hz, 3H). $^{13}$C NMR (100 MHz, CDCl$_3$): δ 206.3, 178.2, 142.5, 131.5, 128.1, 127.2, 119.5, 110.1, 79.1, 72.4, 45.9, 40.7, 37.7, 18.6, 14.1. ESI-HRMS: calcd for C$_{15}$H$_{16}$BrNO$_3$Na (MNa$^+$) 360.0211, found 360.0212. HPLC (Daicel Chiralpak IB, hexane/i-PrOH=90/10, 0.6 mL/min, λ=254 nm): t$_R$ (major diastereomer, major enantiomer, (2'S,6'R)-3ac)=22.7 min, t$_R$ (major diastereomer, minor enantiomer, (2'R,6'S)-3ac)=26.6 min.

Example 4

Product 3ad (2'S,6'R)-5-methyl-6'-propyl-5',6'-dihydrospiro[indoline-3,2'-pyran]-2,4'(3'H)-dione (3ad Major Diastereomer)

The title compound was prepared in analogy to Example 1 from enone 1a and isatin 2d by use of amine A, acid J, and thiourea O.

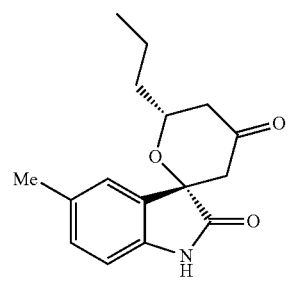 [SMILES: CCC[C@@H]1CC(=O)C[C@@]2(O1)C(=O)Nc1ccc(C)cc12]

Pale yellow gum. [α]$^{20}_D$ +90.0 (c 0.90, CH$_2$Cl$_2$, 93% ee). $^1$H NMR (400 MHz, CDCl$_3$): δ 8.37 (s, 1H), 7.10 (d, J=7.6 Hz, 1H), 6.97 (s, 1H), 6.84 (d, J=7.6 Hz, 1H), 4.33 (m, 1H), 3.07 (d, J=14.4 Hz, 1H), 2.69-2.60 (m, 2H), 2.40 (d, J=14.4 Hz, 1H), 2.31 (s, 3H), 1.78-1.69 (m, 1H), 1.60-1.52 (m, 1H), 1.45-1.25 (m, 2H), 0.85 (t, J=7.2 Hz, 3H). $^{13}$C NMR (100 MHz, CDCl$_3$): δ 205.9, 175.4, 138.2, 132.7, 130.9, 128.7, 126.5, 111.0, 79.2, 73.3, 48.0, 45.8, 38.7, 21.4, 18.5, 14.1. ESI-HRMS: calcd for C$_{16}$H$_{19}$NO$_3$Na (MNa$^+$) 296.1263, found 296.1264. HPLC (Daicel Chiralpak IB, hexane/i-PrOH=90/10, 0.6 mL/min, λ=254 nm): t$_R$ (major diastereomer, major enantiomer, (2'S,6'R)-3ad)=16.1 min, t$_R$ (major diastereomer, minor enantiomer, (2'R,6'S)-3ad)=18.5 min.

Example 5

Product 3ae (2'S,6'R)-5-bromo-6'-propyl-5',6'-dihydrospiro[indoline-3,2'-pyran]-2,4'(3'H)-dione (3ae Major Diastereomer)

The title compound was prepared in analogy to Example 1 from enone 1a and isatin 2e by use of amine A, acid J, and thiourea O.

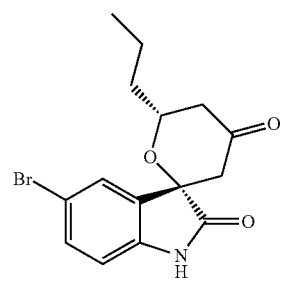 [SMILES: CCC[C@@H]1CC(=O)C[C@@]2(O1)C(=O)Nc1ccc(Br)cc12]

Pale yellow amorphous solid. [α]$^{20}_D$ +55.2 (c 0.87, CH$_2$Cl$_2$, 86% ee). $^1$H NMR (400 MHz, CDCl$_3$): δ 9.03 (s, 1H), 7.45 (dd, J=8.0 Hz, 2.0 Hz, 1H), 7.30 (d, J=2.0 Hz, 1H), 6.87 (d, J=8.0 Hz, 1H), 4.31-4.28 (m, 1H), 3.04 (d, J=14.4 Hz, 1H), 2.71-2.60 (m, 2H), 2.45 (d, J=14.4 Hz, 1H), 1.78-1.68 (m, 1H), 1.60-1.53 (m, 1H), 1.45-1.26 (m, 2H), 0.86 (t, J=7.6 Hz, 3H). $^{13}$C NMR (100 MHz, CDCl$_3$): δ 204.8, 175.3, 139.5, 133.3, 130.4, 128.3, 115.5, 112.6, 78.8, 73.4, 47.4, 45.5, 38.3, 19.1, 18.1. ESI-HRMS: calcd for C$_{15}$H$_{16}$BrNO$_3$Na (MNa$^+$) 360.0211, found 360.0215. HPLC (Daicel Chiralpak IB, hexane/i-PrOH=90/10, 1.0 mL/min, λ=254 nm): t$_R$ (major diastereomer, major enantiomer, (2'S,6'R)-3ae)=11.7 min, t$_R$ (major diastereomer, minor enantiomer, (2'R,6'S)-3ae)=14.0 min Product (2'S*,6'S*)-3ae (minor diastereomer). $^1$H NMR (400 MHz, CDCl$_3$): 4.89-4.82 (m, 1H, CH$_2$CHO).

Example 6

Product 3af (2'S,6'R)-6-chloro-6'-propyl-5',6'-dihydrospiro[indoline-3,2'-pyran]-2,4'(3'H)-dione (3af Major Diastereomer)

The title compound was prepared in analogy to Example 1 from enone 1a and isatin 2f by use of amine A, acid J, and thiourea O.

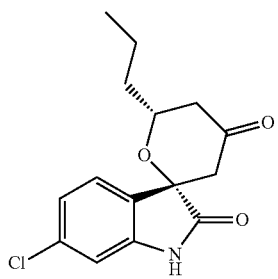 [SMILES: CCC[C@@H]1CC(=O)C[C@@]2(O1)C(=O)Nc1cc(Cl)ccc12]

Pale yellow gum. [α]$^{20}_D$ +78.2 (c 0.61, CH$_2$Cl$_2$, 90% ee). $^1$H NMR (400 MHz, CDCl$_3$): δ 8.99 (s, 1H), 7.10 (d, J=8.4, Hz, 1H), 7.02-7.00 (m, 2H), 4.30-4.24 (m, 1H), 3.07 (d, J=14.0 Hz, 1H), 2.71-2.59 (m, 2H), 2.40 (dd, J=14.0 Hz, 1.2 Hz, 1H), 1.78-1.69 (m, 1H), 1.59-1.51 (m, 1H), 1.42-1.25 (m, 2H), 0.84 (t, J=7.6 Hz, 3H). $^{13}$C NMR (100 MHz, CDCl$_3$): δ 205.2, 175.5, 141.8, 136.3, 126.7, 126.3, 122.8, 111.8, 78.5, 73.3, 47.6, 45.3, 38.3, 18.2, 13.7. ESI-HRMS: calcd for C$_{15}$H$_{16}$ClNO$_3$Na (MNa$^+$) 316.0716, found 316.0718. HPLC (Daicel Chiralpak IB, hexane/i-PrOH=90/10, 1.0 mL/min, λ=254 nm): t$_R$ (major diastereomer, major enantiomer, (2'S,6'R)-3af)=11.8 min, t$_R$ (major diastereomer, minor enantiomer, (2'R,6'S)-3ae)=13.2 min.

Product (2'S*,6'S*)-3af (minor diastereomer). $^1$H NMR (400 MHz, CDCl$_3$): δ 4.88-4.80 (m, 1H, CH$_2$CHO) ppm.

Example 7

Product 3ba (2'S,6'R)-6'-hexyl-5',6'-dihydrospiro[indoline-3,2'-pyran]-2,4'(3'H)-dione (3ba Major Diastereomer)

The title compound was prepared in analogy to Example 1 from enone 1b and isatin 2a by use of amine A, acid J, and thiourea O.

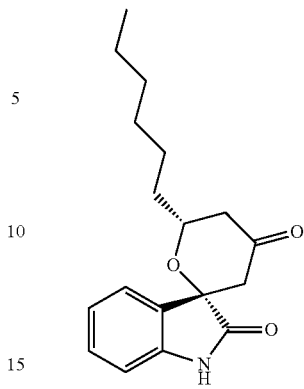

Pale yellow gum. [α]$^{20}_D$ +72.9 (c 0.70, CH$_2$Cl$_2$, 91% ee). $^1$H NMR (400 MHz, CDCl$_3$): δ 8.82 (s, 1H), 7.31 (ddd, J=8.0 Hz, 7.6 Hz, 0.8 Hz, 1H), 7.18 (d, J=7.2 Hz, 1H), 7.02 (ddd, J=7.6 Hz, 7.2 Hz, 0.8 Hz, 1H), 6.97 (d, J=8.0 Hz, 1H), 4.34-4.30 (m, 1H), 3.09 (d, J=14.0 Hz, 1H), 2.66-2.64 (m, 2H), 2.41 (d, J=14.0 Hz, 1H), 1.75-1.72 (m, 1H), 1.61-1.55 (m, 1H), 1.36-1.18 (m, 8H), 0.83 (t, J=6.8 Hz, 3H). $^{13}$C NMR (100 MHz, CDCl$_3$): δ 205.5, 175.5, 140.5, 130.3, 128.3, 125.5, 122.8, 111.1, 78.9, 73.4, 47.7, 45.5, 36.3, 31.6, 28.9, 24.8, 22.5, 14.0. ESI-HRMS: calcd for C$_{18}$H$_{23}$NO$_3$Na (MNa$^+$) 324.1576, found 324.1573. HPLC (Daicel Chiralpak IB, hexane/i-PrOH=90/10, 1.0 mL/min, λ=254 nm): t$_R$ (major diastereomer, major enantiomer, (2'S,6'R)-3ba)=9.9 min, t$_R$ (major diastereomer, minor enantiomer, (2'R,6'S)-3ba)= 11.0 min.

Product (2'S*,6'S*)-3ba (minor diastereomer). $^1$H NMR (400 MHz, CDCl$_3$): 4.90-4.82 (m, 1H, CH$_2$CHO).

Example 8

Product 3ca (2'S,6'S)-6'-isopropyl-5',6'-dihydrospiro[indoline-3,2'-pyran]-2,4'(3'H)-dione (3ca Major Diastereomer)

The title compound was prepared in analogy to Example 1 from enone 1c and isatin 2a by use of amine A, acid J, and thiourea O.
Pale yellow gum.

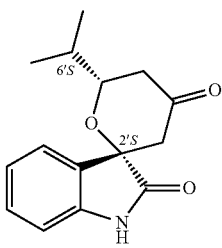 [SMILES: CC(C)[C@@H]1CC(=O)C[C@@]2(O1)C(=O)Nc1ccccc12]

[α]$^{20}_D$ +90.3 (c 0.70, CH$_2$Cl$_2$, 93% ee). $^1$H NMR (400 MHz, CDCl$_3$): δ 8.97 (s, 1H), 7.27 (dt, J=7.6, 1.2 Hz, 1H), 7.15 (d, J=7.6 Hz, 1H), 7.00 (dt, J=7.6, 1.2 Hz, 1H), 6.94 (d, J=7.6 Hz, 1H), 4.01 (m, 1H), 3.04 (d, J=14.4 Hz, 1H), 2.65-2.57 (m, 2H), 2.40 (dd, J=14.4, 1.2 Hz, 1H), 1.88-1.76 (m, 1H), 0.89 (d, J=6.8 Hz, 3H), 0.83 (d, J=6.8 Hz, 3H). $^{13}$C NMR (100 MHz, CDCl$_3$): δ 206.1, 175.7, 140.6, 130.3, 128.4, 125.4, 122.8, 111.1, 78.7, 77.9, 45.4, 44.7, 33.2, 18.3, 17.6.

ESI-HRMS: calcd for $C_{15}H_{17}NO_3Na$ (MNa$^+$) 282.1106, found 282.1100. HPLC (Daicel Chiralpak IB, hexane/i-PrOH=95/5, 0.6 mL/min, λ=254 nm): $t_R$ (major diastereomer, major enantiomer, (2'S,6'S)-3ca)=32.8 min, $t_R$ (major diastereomer, minor enantiomer, (2'R,6'R)-3ca)=36.9 min, $t_R$ (minor diastereomers)=30.7 min and 35.2 min.

Product 3ca [(2'S,6'S)-3ca/(2'S*,6'R*)-3ca=2.2:1]. $^1$H NMR (400 MHz, CDCl$_3$, * donates (2'S*,6'R*)-3ca): δ 8.97 (s, 1H×2.2/3.2), 8.57 (s, 1H*×1/3.2), 7.36-6.89 (4H), 4.65 (m, 1H*×1/3.2), 4.01 (m, 1H×2.2/3.2), 3.04 (d, J=14.4 Hz, 1H×2.2/3.2), 2.77 (d, J=14.8 Hz, 1H*×1/3.2), 2.67-2.40 (3H), 1.98-1.76 (m, 1H), 0.95-0.83 (6H). $^{13}$C NMR (100 MHz, CDCl$_3$, *donates (2'S*,6'R*)-3ca): δ 206.2, 205.3*, 177.1*, 175.6, 140.6, 140.3*, 130.3, 129.5*, 128.4, 125.4, 124.2*, 123.3*, 122.7, 111.1, 110.5*, 78.7, 48.0, 76.2*, 45.7*, 45.5, 44.7, 43.6*, 33.2, 33.1*, 18.3, 18.1*, 17.6, 17.3*.

Product (2'S*,6'R*)-3ca (minor diastereomer). (signals used for the determination of dr): $^1$H NMR (400 MHz, CDCl$_3$): δ 4.65 (m, 1H, CH$_2$CHO).

Example 9

Product 3da (2'S,6'R)-6'-phenethyl-5',6'-dihydrospiro[indoline-3,2'-pyran]-2,4'(3'H)-dione (3da Major Diastereomer)

The title compound was prepared in analogy to Example 1 from enone 1d and isatin 2a by use of amine A, acid J, and thiourea O.

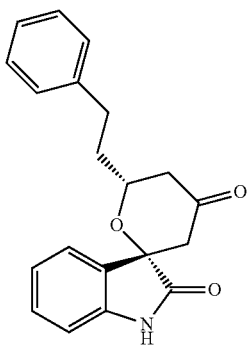 [SMILES: O=C1C[C@@H](CCc2ccccc2)O[C@]2(C1)C(=O)Nc1ccccc12]

Pale yellow gum. [α]$^{20}_D$ +101.3 (c 0.98, CH$_2$Cl$_2$, 91% ee). $^1$H NMR (400 MHz, CDCl$_3$): δ 9.22 (s, 1H), 7.33 (t, J=7.6 Hz, 1H), 7.12-7.08 (m, 3H), 7.03 (t, J=7.6 Hz, 2H), 6.97 (t, J=7.6 Hz, 1H), 6.93-6.90 (m, 2H), 4.25 (m, 1H), 3.11 (d, J=14.0 Hz, 1H), 2.74-2.53 (m, 4H), 2.42 (dd, J=14.0 Hz, 1.6 Hz, 1H), 2.10 (m, 1H), 1.80 (m, 1H). $^{13}$C NMR (100 MHz, CDCl$_3$): δ 205.2, 175.7, 140.9, 140.6, 130.4, 128.5, 128.3, 128.2, 125.9, 125.6, 122.8, 111.2, 79.0, 71.6, 47.7, 45.3, 37.8, 31.0. ESI-HRMS: calcd for $C_{20}H_{19}NO_3Na$ (MNa$^+$) 344.1263, found 344.1259. HPLC (Daicel Chiralpak IB, hexane/i-PrOH=90/10, 0.6 mL/min, λ=254 nm): $t_R$ (major diastereomer, major enantiomer, (2'S,6'R)-3da)=25.3 min, $t_R$ (major diastereomer, minor enantiomer, (2'R,6'S)-3da)=29.6 min, $t_R$ (minor diastereomers)=26.9 min and 33.4 min.

Product (2'S*,6'S*)-3da (minor diastereomer). $^1$H NMR (400 MHz, CDCl$_3$): δ 4.94-4.86 (m, 1H, CH$_2$CHO).

Example 10

Product 3ea (2'S,6'R)-(but-3-yn-1-yl)-5',6'-dihydrospiro[indoline-3,2'-pyran]-2,4'(3'H)-dione (3ea Major Diastereomer)

The title compound was prepared in analogy to Example 1 from enone 1e and isatin 2a by use of amine A, acid J, and thiourea O.

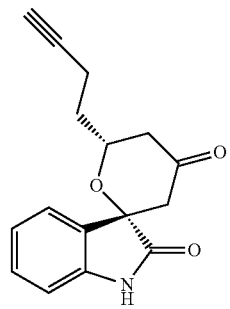 [SMILES: C#CCC[C@@H]1CC(=O)C[C@@]2(O1)C(=O)Nc1ccccc12]

Pale yellow gum. [α]$^{20}_D$ +110.6 (c 0.86, CH$_2$Cl$_2$, 92% ee). $^1$H NMR (400 MHz, CDCl$_3$): δ 8.97 (s, 1H), 7.31 (dt, J=7.6 Hz, 0.8 Hz, 1H), 7.21 (d, J=7.6 Hz, 1H), 7.02 (dt, J=7.6, 0.8 Hz, 1H), 6.97 (d, J=7.6 Hz, 1H), 4.54 (m, 1H), 3.08 (d, J=14.4 Hz, 1H), 2.75-2.63 (m, 2H), 2.47 (dd, J=14.4 Hz, 1.2 Hz, 1H), 2.27-2.20 (m, 2H), 2.02-1.91 (m, 1H), 1.82 (t, J=2.4 Hz, 1H), 1.81-1.74 (m, 1H). $^{13}$C NMR (100 MHz, CDCl$_3$): δ 204.8, 175.5, 140.5, 130.4, 128.1, 125.5, 122.8, 111.1, 82.9, 78.9, 71.6, 69.0, 47.3, 45.4, 34.6, 14.4. ESI-HRMS: calcd for $C_{16}H_{15}NO_3Na$ (MNa$^+$) 292.0950, found 292.0947. HPLC (Daicel Chiralpak IB, hexane/i-PrOH=90/10, 1.0 mL/min, λ=254 nm): $t_R$ (major diastereomer, major enantiomer, (2'S,6'R)-3ea)=16.6 min, $t_R$ (major diastereomer, minor enantiomer, (2'R,6'S)-3ea)=18.6 min.

Product (2'S*,6'S*)-3ea (minor diastereomer). $^1$H NMR (400 MHz, CDCl$_3$): δ 5.06-4.98 (m, 1H, CH$_2$CHO).

Example 11

Product 3fa (2'S,6'R)-6'-(but-3-en-1-yl)-5',6'-dihydrospiro[indoline-3,2'-pyran]-2,4'(3'H)-dione (3fa Major Diastereomer)

The title compound was prepared in analogy to Example 1 from enone 1f and isatin 2a by use of amine A, acid J, and thiourea O.

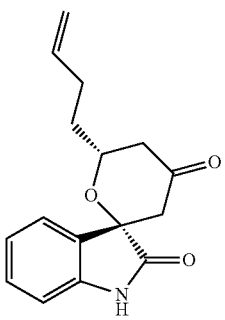 [SMILES: C=CCC[C@@H]1CC(=O)C[C@@]2(O1)C(=O)Nc1ccccc12]

Pale yellow gum. $[\alpha]^{20}{}_D$ +87.2 (c 0.66, $CH_2Cl_2$, 93% ee). $^1H$ NMR (400 MHz, $CDCl_3$): δ 9.12 (s, 1H), 7.31 (dt, J=8.0 Hz, 1.2 Hz, 1H), 7.17 (d, J=7.2 Hz, 1H), 7.04-6.97 (m, 2H), 5.67 (ddt, J=17.2 Hz, 10.4 Hz, 6.4 Hz, 1H), 4.88-4.82 (m, 2H), 4.39-4.32 (m, 1H), 3.10 (d, J=14.0 Hz, 1H), 2.72-2.60 (m, 2H), 2.44 (dd, J=14.0 Hz, 1.2 Hz, 1H), 2.19-2.00 (m, 2H), 1.91-1.82 (m, 1H), 1.69-1.60 (m, 1H). $^{13}C$ NMR (100 MHz, $CDCl_3$): δ 205.2, 175.6, 140.6, 137.2, 130.4, 128.2, 125.5, 122.8, 115.4, 111.1, 78.9, 72.4, 47.6, 45.4, 35.2, 29.1. ESI-HRMS: calcd for $C_{16}H_{17}NO_3Na$ ($MNa^+$) 294.1106, found 294.1120. HPLC (Daicel Chiralpak IB, hexane/i-PrOH=90/10, 1.0 mL/min, λ=254 nm): $t_R$ (major diastereomer, major enantiomer, (2'S,6'R)-3fa)=12.3 min, $t_R$ (major diastereomer, minor enantiomer, (2'R,6'S)-3fa)=13.6 min.

Product (2'S*,6'S*)-3fa (minor diastereomer). $^1H$ NMR (400 MHz, $CDCl_3$): δ 8.80 (s, 1H, CONH).

Example 12

Product 3ga (2'S,6'R)-6'-(2-(1,3-dioxoisoindolin-2-yl)ethyl)-5',6'-dihydrospiro[indoline-3,2'-pyran]-2,4'(3'H)-dione (3ga Major Diastereomer)

The title compound was prepared in analogy to Example 1 from enone 1 g and isatin 2a by use of amine A, acid J, and thiourea O.

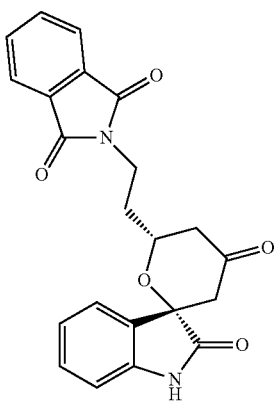 [SMILES: O=C1C[C@@H](CCN2C(=O)c3ccccc3C2=O)O[C@]2(C1)C(=O)Nc1ccccc12]

Colorless solid; mp: 199-201 (91% ee). $[\alpha]^{20}{}_D$ +67.7 (c 0.74, $CH_2Cl_2$, 91% ee). $^1H$ NMR (400 MHz, $CDCl_3$): δ 8.21 (brs, 1H), 7.73-7.64 (m, 4H), 7.24 (dt, J=7.6 Hz, 1.2 Hz, 1H), 7.05 (d, J=7.6 Hz, 1H), 6.92 (d, J=7.6 Hz, 1H), 6.84 (dt, J=7.6 Hz, 0.8 Hz, 1H), 4.38 (m, 1H), 3.82 (dt, J=14.0, 6.8 Hz, 1H), 3.72 (dt, J=14.0, 6.8 Hz, 1H), 3.05 (d, J=14.4 Hz, 1H), 2.74 (dd, J=14.4 Hz, 11.2 Hz, 1H), 2.61 (ddd, J=14.4 Hz, 2.4 Hz, 1.6 Hz, 1H), 2.39 (dd, J=14.4 Hz, 1.6 Hz, 11-1), 2.22-2.13 (m, 1H), 2.09-2.02 (m, 1H). $^{13}C$ NMR (100 MHz, $CDCl_3$): δ 204.5, 174.5, 168.1, 140.5, 133.8, 131.8, 130.4, 127.8, 125.4, 123.2, 122.6, 110.9, 78.7, 70.9, 47.3, 45.3. ESI-HRMS: calcd for $C_{22}H_{18}N_2O_5Na$ ($MNa^+$) 413.1113, found 413.1105. HPLC (Daicel Chiralpak IB, hexane/i-PrOH=90/10, 0.6 mL/min, λ=254 nm): $t_R$ (major diastereomer, major enantiomer, (2'S,6'R)-3ga)=23.9 min, $t_R$ (major diastereomer, minor enantiomer, (2'R,6'S)-3ga)=32.8 min.

Example 13

Product 3ha (2'S,6'R)-6'-(3-((tert-butyldimethylsilyl)oxy)propyl)-5',6'-dihydrospiro[indoline-3,2'-pyran]-2,4'(3'H)-dione (3ha Major Diastereomer)

The title compound was prepared in analogy to Example 1 from enone 1 h and isatin 2a by use of amine A, acid J, and thiourea O.

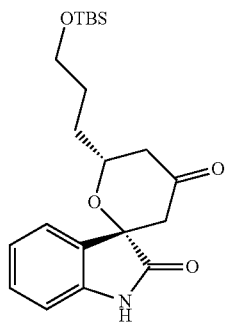 [SMILES: CC(C)(C)[Si](C)(C)OCCC[C@@H]1CC(=O)C[C@@]2(O1)C(=O)Nc1ccccc12]

Pale yellow gum. $[\alpha]^{20}{}_D$ +70.2 (c 1.32, $CH_2Cl_2$, 92% ee). $^1H$ NMR (400 MHz, $CDCl_3$): δ 8.84 (s, 1H), 7.28 (dt, J=7.6 Hz, 0.8 Hz, 1H), 7.17 (d, J=7.6 Hz, 1H), 7.01 (dt, J=7.6 Hz, 0.8 Hz, 1H), 6.96 (d, J=7.6 Hz, 1H), 4.38-4.31 (m, 1H), 3.51 (t, J=6.4 Hz, 2H), 3.08 (d, J=14.0 Hz, 1H), 2.67-2.64 (m, 2H), 2.41 (d, J=14.0 Hz, 1H), 1.80-1.45 (m, 4H), 0.84 (s, 9H), −0.02 (s, 6H). $^{13}C$ NMR (100 MHz, $CDCl_3$): δ 205.4, 175.7, 140.6, 130.4, 128.2, 125.4, 122.8, 111.1, 78.9, 73.1, 62.5, 47.7, 45.5, 32.7, 28.2, 25.9, 18.3, −5.39. ESI-HRMS: calcd for $C_{21}H_{31}NO_4SiNa$ ($MNa^+$) 412.1920, found 412.1915. HPLC (Daicel Chiralpak IB, hexane/i-PrOH=90/10, 1.0 mL/min, λ=254 nm): $t_R$ (major diastereomer, major enantiomer, (2'S,6'R)-3ha)=8.63 min, $t_R$ (major diastereomer, minor enantiomer, (2'R,6'S)-3ha)=9.19 min.

Product (2'S*,6'S*)-3ha (minor diastereomer). $^1H$ NMR (400 MHz, $CDCl_3$): 4.96-4.88 (m, 1H, $CH_2CHO$).

Example 14

Product 3ia (2'S,6'R)-6'-(3-chloropropyl)-5',6'-dihydrospiro[indoline-3,2'-pyran]-2,4'(3'H)-dione (3ia Major Diastereomer)

The title compound was prepared in analogy to Example 1 from enone 1i and isatin 2a by use of amine A, acid J, and thiourea O.

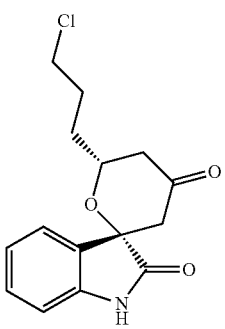 [SMILES: O=C1C[C@@H](CCCCl)O[C@]2(C1)C(=O)Nc1ccccc12]

Pale yellow gum. [α]$^{20}_D$ +81.1 (c 1.0, CH$_2$Cl$_2$, 93% ee). $^1$H NMR (400 MHz, CDCl$_3$): δ 8.98 (s, 1H), 7.32 (dt, J=7.6 Hz, 0.8 Hz, 1H), 7.18 (d, J=7.6 Hz, 1H), 7.03 (t, J=7.6 Hz, 1H), 6.99 (d, J=7.6 Hz, 1H), 4.40-4.34 (m, 1H), 3.46 (t, J=6.4 Hz, 2H), 3.09 (d, J=14.4 Hz, 1H), 2.71 (dd, J=14.4 Hz, 10.8 Hz, 1H), 2.64 (ddd, J=14.4 Hz, 3.2 Hz, 1.6 Hz, 1H), 2.44 (dd, J=14.4 Hz, 1.6 Hz, 1H), 1.94-1.71 (m, 4H). $^{13}$C NMR (100 MHz, CDCl$_3$): δ 204.9, 175.4, 140.5, 130.5, 128.1, 125.4, 122.9, 111.2, 78.9, 72.5, 47.6, 45.4, 44.6, 33.5, 28.1. ESI-HRMS: calcd for C$_{15}$H$_{16}$ClNO$_3$Na (MNa$^+$) 316.0716, found 316.0717. HPLC (Daicel Chiralpak IB, hexane/i-PrOH=80/20, 1.0 mL/min, λ=254 nm): $t_R$ (major diastereomer, major enantiomer, (2'S,6'R)-3ia)=9.6 min, $t_R$ (major diastereomer, minor enantiomer, (2'R,6'S)-3ia)=10.5 min, $t_R$ (minor diastereomers)=9.2 min.

Product (2'S*,6'S*)-3ia (minor diastereomer). $^1$H NMR (400 MHz, CDCl$_3$): 4.94-4.88 (m, 1H, CH$_2$CHO).

Example 15

Product 3ja (2'R,6'R)-6'-phenyl-5',6'-dihydrospiro[indoline-3,2'-pyran]-2,4'(3'H)-dione (3ea Major Diastereomer)

The title compound was prepared in analogy to Example 11 from enone 1j and isatin 2a by use of amine F and acid J.

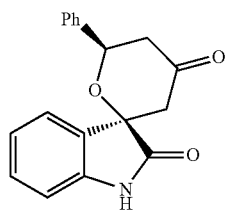 [SMILES: O=C1C[C@H](c2ccccc2)O[C@@]2(C1)C(=O)Nc1ccccc12]

Relative and absolute stereochemistries were assigned by analogy. Rf 0.23 (hexane/EtOAc=2:1). Pale yellow amorphous solid. [α]$^{20}_D$ +18.1 (c 0.6, CH$_2$Cl$_2$, 77% ee). $^1$H NMR (400 MHz, CDCl$_3$): δ 8.18 (s, 1H), 7.43-7.41 (m, 2H), 7.38-7.29 (m, 5H), 7.08 (t, J=7.2 Hz, 1H), 6.96 (d, J=8.4 Hz, 1H), 5.37 (dd, J=11.6 Hz, 2.4 Hz, 1H), 3.22 (d, J=14.8 Hz, 1H), 3.04 (dd, J=14.8 Hz, 11.6 Hz, 1H), 2.87 (ddd, J=14.8 Hz, 2.4 Hz, 1.6 Hz, 1H), 2.59 (dd, J=14.8 Hz, 1.6 Hz, 1H). $^{13}$C NMR (100 MHz, CDCl$_3$): δ 204.7, 174.7, 140.5, 139.8, 130.6, 128.7, 128.4, 128.1, 126.0, 125.4, 122.9, 111.0, 78.9, 75.0, 49.6, 45.1. ESI-HRMS: calcd for C$_{18}$H$_{15}$NO$_3$Na (MNa$^+$) 316.0905, found 316.0944. HPLC (Daicel Chiralpak IA, hexane/i-PrOH=80/20, 0.8 mL/min, λ=254 nm): $t_R$ (major diastereomer, major enantiomer)=21.2 min, $t_R$ (major diastereomer, minor enantiomer)=31.5 min, $t_R$ (minor diastereomers)=15.2 min and 18.0 min.

Product 3ja (minor diastereomer). Rf 0.30 (hexane/EtOAc=2:1). Pale yellow amorphous solid. $^1$H NMR (400 MHz, CDCl$_3$): δ 7.66 (s, 1H), 7.46 (d, J=7.6 Hz, 1H), 7.43-7.41 (m, 2H), 7.34-7.28 (m, 4H), 7.13 (t, J=7.6 Hz, 1H), 6.87 (d, J=8.0 Hz, 1H), 5.95 (dd, J=11.2, 3.2 Hz, 1H), 2.95 (d, J=14.8 Hz, 1H), 2.89-2.84 (m, 1H), 2.74 (dd, J=14.8 Hz, 11.2 Hz, 1H), 2.61 (dd, J=14.8 Hz, 1.6 Hz, 1H). $^{13}$C NMR (100 MHz, CDCl$_3$): δ=203.4, 175.9, 140.6, 140.2, 130.6, 129.0, 128.7, 128.3, 126.0, 124.5, 123.5, 110.3, 78.2, 73.6, 48.8, 45.6.

Example 16

Product 5

(2'S,4'R,6'R)-4'-hydroxy-6'-propyl-3',4',5',6'-tetrahydrospiro[indoline-3,2'-pyran]-2-one (5 Major Enantiomer)

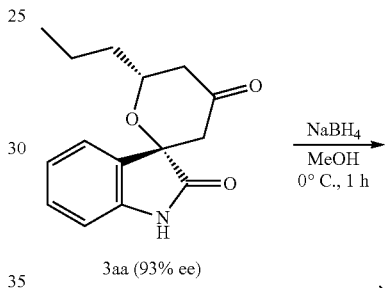

To a solution of 3aa (93% ee, 27.0 mg, 0.10 mmol) in MeOH (1.0 mL) was added NaBH$_4$ (7.9 mg, 0.21 mmol) at 0° C. and the mixture was stirred at the same temperature for 1 h (consumption of 3aa was analyzed by TLC). Acetic acid (30 μL) was added to the mixture at same temperature and the solvent was removed in vacuo. The residue was purified by flash column chromatography (hexane/EtOAc=2:1) to give 5 (19.6 mg, 72%, single diastereomer, 92% ee). Colorless solid; mp: 169-171. [α]$^{20}_D$ +56.0 (c 0.94, CH$_2$Cl$_2$, 92% ee). $^1$H NMR (400 MHz, CDCl$_3$): δ 8.10 (d, J=7.6 Hz, 1H), 7.97 (s, 1H), 7.23 (dd, J=7.6 Hz, 1.2 Hz, 1H), 7.03 (td, J=7.6 Hz, 1.2 Hz, 1H), 6.87 (d, J=7.6 Hz, 1H), 4.53 (m, 1H), 4.35 (m, 1H), 2.36 (dd, J=14.4 Hz, 3.6 Hz, 1H), 1.85-1.82 (m, 2H), 1.74 (dd, J=14.4, 2.0 Hz, 1H), 1.70 (d, J=2.0 Hz, 1H), 1.59-1.52 (m, 1H), 1.44-1.20 (m, 3H), 0.81 (t, J=7.2 Hz, 3H). $^{13}$C NMR (100 MHz, CDCl$_3$): δ=177.6, 140.5, 131.0, 129.2, 127.9, 122.5, 110.1, 77.2, 66.8, 64.3, 38.0, 37.4, 36.0, 18.4, 13.9. ESI-HRMS: calcd for C$_{15}$H$_{19}$NO$_3$Na (MNa$^+$) 284.1263, found 284.1259. HPLC (Daicel Chiralpak IB, hexane/i-PrOH=90/10, 0.6 mL/min, λ=254 nm): $t_R$ (major enantiomer, (2'S,4'R,6'R)-5)=25.2 min, $t_R$ (minor enantiomer)=23.2 min.

Configuration at the 4'-position of 5 was determined based on the relative stereochemistry analyzed by NOESY experiments.

Example 17

Product 6

(2'S,4'R,6'R)-4'-(benzylamino)-6-propyl-3',4',5',6-tetrahydrospiro[indoline-3,2'-pyran]-2-one (6 Major Enantiomer)

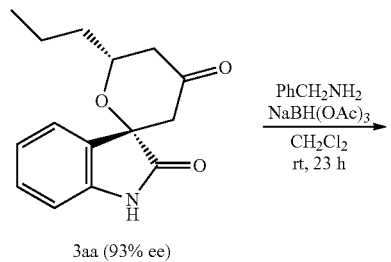

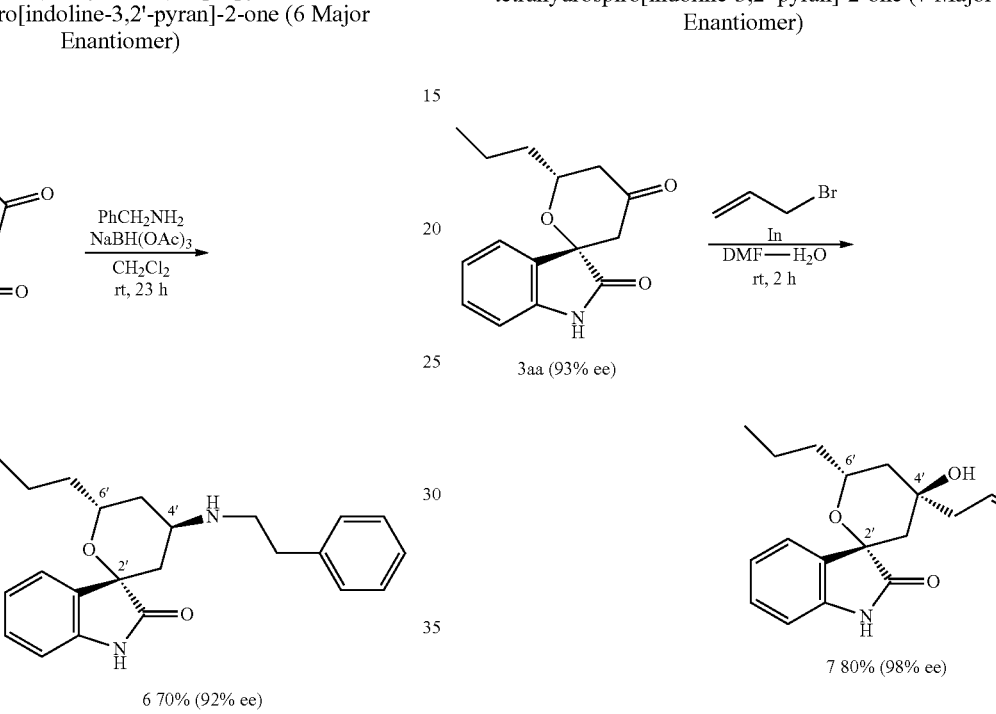

To a solution of 3aa (93% ee, 20.0 mg, 0.077 mmol) in CH$_2$Cl$_2$ (1.5 mL) were added benzylamine (25.1 µL, 0.23 mmol) and NaBH(OAc)$_3$ (49.1 mg, 0.23 mmol). The mixture was stirred at room temperature for 23 h (consumption of 3aa was analyzed by TLC). After addition of aqueous NaOH (1 N, 0.5 mL), the mixture was extracted with CH$_2$Cl$_2$ (×3), washed with brine, dried over Na$_2$SO$_4$, filtered, and concentrated. The residue was purified by flash column chromatography (hexane/EtOAc=1:1) gave 6 (18.8 mg, 70%, single diastereomer, 92% ee). Pale yellow gum. [α]$^{20}_D$ −5.2 (c 0.93, CH$_2$Cl$_2$, 92% ee). $^1$H NMR (400 MHz, CDCl$_3$): δ 8.35, (s, 1H), 8.34 (d, J=7.6 Hz, 1H), 7.37-7.27 (m, 5H), 7.23 (dt, J=7.6 Hz, 0.8 Hz, 1H), 7.03 (dt, J=7.6 Hz, 0.8 Hz, 1H), 6.87 (d, J=7.6 Hz, 1H), 4.38-4.31 (m, 1H), 3.74 (d, J=12.4 Hz, 1H), 3.70 (d, J=12.4 Hz, 1H), 3.46 (quintet, J=4.0 Hz, 1H), 2.28 (dd, J=14.4 Hz, 4.0 Hz, 1H), 1.88 (ddd, J=14.0 Hz, 10.8 Hz, 4.0 Hz, 1H), 1.78 (ddd, J=14.4 Hz, 4.0 Hz, 1.2 Hz, 1H), 1.69 (d, J=14.4 Hz, 1H), 1.59-1.52 (m, 2H), 1.41-1.27 (m, 3H), 0.82 (t, J=7.2 Hz, 3H). $^{13}$C NMR (100 MHz, CDCl$_3$): δ 178.4, 140.4, 140.3, 131.6, 129.0, 128.5, 128.2, 128.1, 127.1, 122.4, 110.0, 77.7, 67.9, 52.1, 49.7, 38.1, 36.2, 33.4, 18.6, 13.9. ESI-HRMS: calcd for C$_{22}$H$_{27}$N$_2$O$_2$ (MH$^+$) 351.2073, found 351.2068. HPLC (Daicel Chiralpak IA, hexane/i-PrOH=90/10, 1.0 mL/min, λ=254 nm): t$_R$ (major enantiomer, (2'S,4'R,6'R)-6)=16.4 min, t$_R$ (minor enantiomer)=13.9 min. Configuration at the 4'-position of 6 was determined based on the relative stereochemistry analyzed by NOESY experiments.

Example 18

Product 7

(2'S,4'R,6'R)-4'-allyl-4'-hydroxy-6-propyl-3',4',5',6-tetrahydrospiro[indoline-3,2'-pyran]-2-one (7 Major Enantiomer)

A mixture of 3aa (99% ee, 26.0 mg, 0.1 mmol), allylbromide (0.26 mL, 3.0 mmol), and In (45.9 mg, 0.4 mmol) in DMF (0.8 mL)-H$_2$O (0.1 mL) was stirred at room temperature for 2 h. The mixture was added to saturated NH$_4$Cl and extracted with CH$_2$Cl$_2$ (×3). Organic layers were combined and washed with brine, dried with Na$_2$SO$_4$, and concentrated. The residue was purified by flash column chromatography (hexane/EtOAc=1:1) to give 7 (24.1 mg, 80%, single diastereomer, 98% ee). Colorless solid; mp: 189-191. [α]$^{20}_D$ +76.3 (c 0.80, CH$_2$Cl$_2$, 98% ee). $^1$H NMR (400 MHz, CDCl$_3$): δ 8.96 (s, 1H), 8.14 (d, J=8.0 Hz, 1H), 7.22 (td, J=8.0, 1.2 Hz, 1H), 7.00 (dt, J=8.0 Hz, 1.2 Hz, 1H), 6.91 (d, J=8.0 Hz, 1H), 5.88 (m, 1H), 5.25-5.16 (m, 2H), 4.38-4.32 (m, 1H), 2.35 (d, J=14.0 Hz, 1H), 2.30 (d, J=14.0 Hz, 1H), 2.18 (d, J=14.0 Hz, 1H), 1.80 (s, 1H), 1.74 (dt, J=14.0 Hz, 2.0 Hz, 1H), 1.66-1.23 (m, 6H), 0.81 (t, J=7.2 Hz, 3H). $^{13}$C NMR (100 MHz, CDCl$_3$): δ 178.4, 140.8, 132.0, 131.0, 129.1, 128.2, 122.4, 120.7, 110.4, 78.2, 69.8, 68.3, 49.2, 42.0, 40.2, 37.9, 18.5, 13.9. ESI-HRMS: calcd for C$_{18}$H$_{24}$NO$_3$ (MH$^+$) 302.1756, found 302.1768. HPLC (Daicel Chiralpak IA, hexane/i-PrOH=90/10, 1.0 mL/min, λ=254 nm) t$_R$ (major enantiomer, (2'S,4'R,6' R)-7)=14.3 min, t$_R$ (minor enantiomer)=13.5 min. Configuration at the 4'-position of 7 was determined based on the relative stereochemistry analyzed by NOESY experiments.

Example 19

Product 8

4-Methyl-N'-((2'S,6'R)-2-oxo-6'-propyl-5',6'-dihydrospiro[indoline-3,2'-pyran]-4'(3'H)-ylidene)benzenesulfonohydrazide (8 Major Enantiomer)

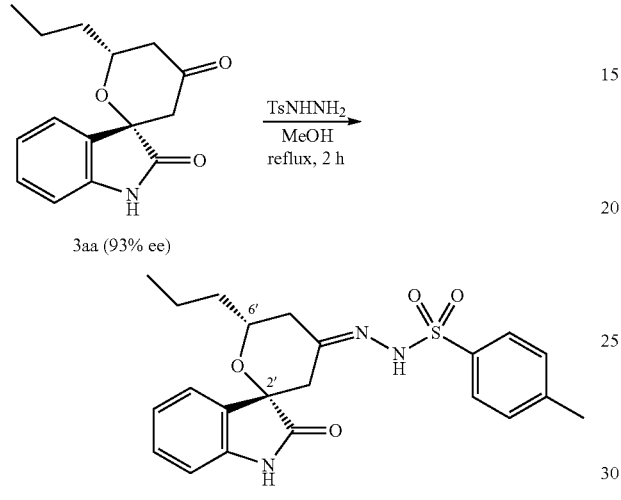

8 82%

A solution of 3aa (93% ee, 59.0 mg, 0.23 mmol) and p-toluenesulfonyl hydrazide (42.8 mg, 0.23 mmol) in MeOH (2.3 mL) was refluxed for 2 h. After being cooled to room temperature, generated precipitate was collected and washed with hexane/EtOAc (10:1) to give 8 (82%). Pale yellow solid; mp 197-199. $[\alpha]^{20}{}_D$ +204.3 (c 0.10, CH$_2$Cl$_2$). $^1$H NMR (400 MHz, DMSO-d$_6$): δ 10.52, (s, 1H), 10.48, (s, 1H), 7.72 (d, J=8.4 Hz, 2H), 7.37 (d, J=8.4 Hz, 2H), 7.20 (t, J=7.6 Hz, 1H), 6.81 (d, J=7.6 Hz, 1H), 6.70 (d, J=7.6 Hz, 1H), 6.58 (t, J=7.6 Hz, 1H), 3.91-3.85 (m, 1H), 3.04 (d, J=14.0 Hz, 1H), 2.62 (d, J=14.0 Hz, 1H), 2.38 (s, 3H), 2.12 (d, J=14.0 Hz, 1H), 2.00 (dd, J=14.0 Hz, 11.6 Hz, 1H), 1.52-1.37 (m, 2H), 1.33-1.13 (m, 2H), 0.77 (t, J=7.2 Hz, 3H). $^{13}$C NMR (100 MHz, DMSO-d$_6$): δ 174.2, 154.4, 143.1, 141.6, 136.1, 129.4, 128.3, 127.4, 125.3, 121.0, 110.2, 99.6, 77.8, 70.6, 38.6, 37.6, 33.6, 21.0, 17.8, 13.7. ESI-HRMS: calcd for C$_{22}$H$_{26}$N$_3$O$_4$S (MH$^+$) 428.1644, found 428.1659.

5. Solvent Systems

Solvent Systems in the Formal Hetero-Dield-Alder Reaction between enone 1a and isatin 2a were screened.

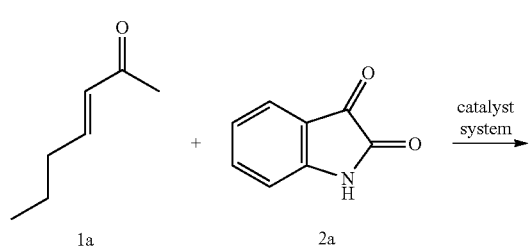

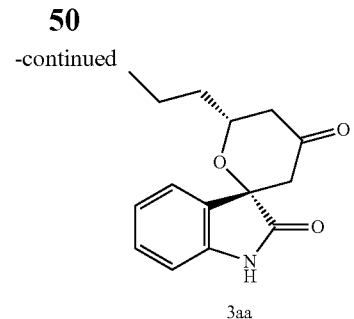
3aa

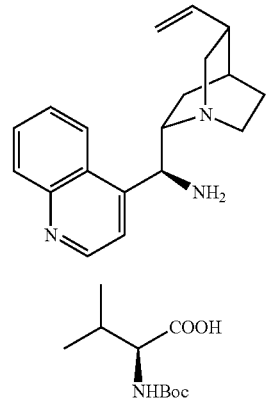

A

I

K

TABLE

| entry | amine | acid | solvent | time (h) | conversion[b] (%) | dr[c] | ee[d] (%) |
|---|---|---|---|---|---|---|---|
| 1 | A | K | toluene | 48 | 78 | 2.0:1 | 83 |
| 2 | A | K | CH$_2$Cl$_2$ | 70 | 45 | 1.1:1 | 75 |
| 3 | A | K | CH$_3$CN | 48 | 44 | 3.2:1 | 46 |
| 4 | A | K | THF | 48 | 42 | 2.6:1 | 63 |
| 5 | A | K | DMF | 48 | <10 | — | — |
| 6[e] | A | I | - (neat) | 48 | 100 | 4.7:1 | 78 |
| 7 | A | I | PhCF$_3$ | 48 | 100 | 4.7:1 | 78 |
| 8 | A | I | 1,3,5-trimethylbenzene | 48 | 88 | 4.7:1 | 82 |
| 9[f] | A | I | toluene | 48 | 90 | 5.2:1 | 84 |

[a] Reaction was performed using enone 1a (0.5 mmol) and isatin 2a (0.1 mmol) in the presence of amine A (0.02 mmol) and acid (0.04 mmol) in solvent (0.2 mL) at 24° C. except as indicated.
[b] Conversion was determined as consumption of 2a based on the ratio of 3aa to 2a; determined by $^1$H NMR.
[c] Diastereomer ratio of 3aa was determined by $^1$H NMR.
[d] Enantiomer excess of the major diastereomer of 3aa was determined by HPLC.
[e] Enone 1a (2.3 mmol, i.e., 0.5 mmol plus 0.2 mL) was used as the solvent.
[f] Table 1, entry 1.

6. Catalyst Systems

Catalyst systems were screened as follows. To a solution of amine (0.02 mmol) and acid (0.04 mmol) in toluene (0.2 mL) were added the thiourea (if used, 0.02 mmol), enone 1 (0.5 mmol) and isatin 2a (0.1 mmol) at room temperature (24° C.). The mixture (initially suspension) was stirred at the same temperature and the progress of the reaction was monitored by TLC. At the indicated time point in the Table, a portion of the mixture (solution) was diluted with CDCl$_3$ and analyzed $^1$H NMR to determine the dr. Remaining portion of the mixture (solution) was applied to a short pad of silica gel and the pad was washed with hexane/EtOAc (2:1) (the amine and acid were removed). The eluted mixture was concentrated (enone 1a was removed with the solvents). The resulting mixture was analyzed by $^1$H NMR to determine the conversion and by HPLC (Daicel Chiralpak IB, hexane/i-PrOH=90:10, 0.6 mL/min, λ=254 nm) to determine the ee of the major diastereomer of 3aa.

| entry | amine | acid + additive | time (h) | conversion (%)[b] | dr[c] | ee (%)[d] |
|---|---|---|---|---|---|---|
| 1 | A | I | 48 | 90 | 5.2:1 | 84 |
| 2 | B | I | 48 | 42 | 5.5:1 | 79 |
| 3 | C | I | 48 | 88 | 3.2:1 | −71 |
| 4 | D | I | 22 | 93 | 1.1:1 | 45 |
| 5 | E | I | 28 | 100 | 2.4:1 | 83 |
| 6 | F | I | 20 | 100 | 8.0:1 | −85 |
| 7 | G | I | 48 | 34 | 1.6:1 | 28 |
| 8 | H | I | 36 | 100 | 1.0:1 | −65 |
| 9 | A | J | 48 | 77 | 11:1 | 87 |
| 10 | A | K | 48 | 78 | 2.0:1 | 83 |
| 11 | A | L | 48 | 71 | 1.7:1 | 15 |
| 12 | A | M | 48 | 75 | 4.6:1 | 79 |
| 13 | A | N | 48 | 76 | 3.8:1 | 77 |
| 14 | F | J | 17 | 100 | 17:1 | −79 |
| 15[e] | A | I | 48 | 53 | 1.8:1 | 31 |
| 16[f] | A | I | 48 | 100 | 5.4:1 | 79 |
| 17[g] | A | J + O | 18 | 100 | 18:1 | 93 |
| 18[h] | A | O | 48 | 100 | 1.0:1 | 62 |
| 19[i] | A | J + O | 48 | 59 | 8.0:1 | 94 |
| 20[g] | F | I + O | 5.5 | 100 | 8.7:1 | −75 |

[a] Reaction was performed using enone 1a (0.5 mmol) and isatin 2a (0.1 mmol) in the presence of amine (0.02 mmol) and acid (0.04 mmol) in toluene (0.2 mL) at 24° C. except as indicated.
[b]Determined by 1H NMR based on the ratio of 3aa to 2a.
[c]Determined by $^1$H NMR.
[d]The major diastereomer of 3aa; determined by HPLC.
[e]Molecular sieves 4 Å were added,
[f]Acid I (0.06 mmol) was used,
[g]Thiourea O (0.02 mmol) was used,
[h]Thiourea O (0.06 mmol) was used,
[i]Amine A (0.01 mmol), acid J (0.02 mmol), and thiourea O (0.01 mmol) were used.

The invention claimed is:

1. A compound of formula I:

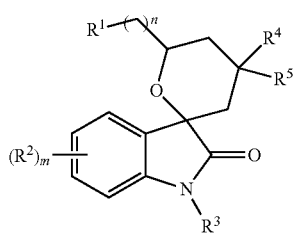

I wherein
$R^1$ is hydrogen, halogen;
lower alkyl, lower cycloalkyl, lower alkenyl, lower alkynyl, lower alkoxy wherein these substituents are optionally substituted with halogen;
cyano, nitro; hydroxyl optionally protected with an appropriate protective group; amino optionally protected with an appropriate protective group,
aryl, heteroaryl wherein these substituents are optionally substituted with
halogen;
lower alkyl, lower alkoxy wherein these substituents are optionally substituted with halogen; or cyano;
—C(=O)OR$^a$, —C(=O)NR$^a$R$^b$, —OC(=O)R$^a$, —OC(=O)OR$^a$, —OC(=O)NR$^a$R$^b$, —NHC(=O)NR$^a$R$^b$, —N{C(=O)R$^a$} {C(=O)R$^b$};

$R^a$ and $R^b$ are each independently hydrogen; lower alkyl, lower cycloalkyl, lower alkenyl, lower alkynyl wherein these substituents are optionally substituted with halogen;
$R^a$ and $R^b$ together form —(CH$_2$)$_l$—, or
$R^a$ and $R^b$ taken together with the nitrogen atom to which they are attached, form heteroaryl
$R^2$ is, each independently, hydrogen, halogen, hydroxyl; lower alkyl, lower alkoxy wherein these substituents are optionally substituted with halogen,
$R^3$ is hydrogen; lower alkyl, lower cycloalkyl wherein these substituents are optionally substituted with halogen or oxo;
lower alkyl-sulfonyl, aryl-sulfonyl;
N-protecting group;
aryl, heteroaryl wherein these substituents are optionally substituted with alkyl, alkoxy, halogen, or hydroxyl;
$R^4$ and $R^5$ are each independently hydrogen, lower alkyl, lower alkenyl, lower alkynyl, lower alkoxy, hydroxyl optionally protected with an appropriate protective group, or amino optionally protected with an appropriate protective group, —NR$^a$R$^b$,
$R^4$ and $R^5$ taken together with the carbon atom to which they are attached, form carbonyl (C=O), oxime (C=NOR$^c$), hydrazone (C=N—NR$^c$R$^d$), acetal (C(OR$^c$)OR$^d$),
$R^c$ and $R^d$, are each independently hydrogen, lower alkyl, lower alkenyl, lower alkynyl, N-protecting group, or O-protecting group;
n is 0 to 12,
m is 0 to 4,
l is 2 to 8
or racemate, enantiomer, diastereomer, mixture thereof, or pharmaceutically acceptable salt thereof.

2. The compound of formula I according to claim 1, wherein
$R^1$ is hydrogen, halogen;
lower alkyl, lower alkenyl, lower alkynyl, lower alkoxy wherein these substituents are optionally substituted with halogen;
cyano, nitro, hydroxyl optionally protected with an appropriate protective group, amino optionally protected with an appropriate protective group aryl which is optionally substituted with
halogen;
lower alkyl, lower alkoxy wherein these substituents are optionally substituted with halogen or cyano;
—C(=O)OR$^a$, —C(=O)NR$^a$R$^b$, —N{C(=O)R$^a$} {C(=O)R$^b$};
$R^a$ and $R^b$ are each independently hydrogen; lower alkyl, lower cycloalkyl, lower alkenyl, lower alkynyl wherein these substituents are optionally substituted with halogen;
$R^a$ and $R^b$ taken together with the nitrogen atom to which they are attached, form heteroaryl
$R^2$ is, each independently, hydrogen, halogen hydroxyl; lower alkyl, lower alkoxy wherein these substituents are optionally substituted with halogen,
$R^3$ is hydrogen; lower alkyl, lower cycloalkyl which is optionally substituted with halogen or oxo; lower alkyl-sulfonyl, aryl-sulfonyl; or N-protecting group;
$R^4$ and $R^5$ are each independently hydrogen, lower alkyl, lower alkenyl, lower alkynyl, lower alkoxy, hydroxyl optionally protected with an appropriate protective group, amino optionally protected with an appropriate protective group, R⁴ and R⁵ taken together with the carbon atom to which they are attached, form carbonyl (C=O), oxime (C=NOR$^c$), hydrazone (C=N—NR$^c$R$^d$)

R$^c$ and R$^d$ are each independently hydrogen, lower alkyl, lower alkenyl, lower alkynyl, O-protecting group, N-protecting group;

n is 0 to 8, m is 0 to 4, l is 2 to 4 or racemate, enantiomer, diastereomer, mixture thereof, or pharmaceutically acceptable salt thereof.

3. The compound of formula I according to claim 1, wherein

R¹ is hydrogen, halogen;

lower alkyl, lower alkenyl, lower alkynyl, lower alkoxy wherein these substituents are optionally substituted with halogen;

hydroxyl optionally protected with an appropriate protective group, amino optionally protected with an appropriate protective group aryl which is optionally substituted with halogen;

lower alkyl, lower alkoxy wherein these substituents are optionally substituted with halogen; or cyano;

—C(=O)OR$^a$, —C(=O)NR$^a$R$^b$, —N{C(=O)R$^a$}{C(=O)R$^b$};

R$^a$ and R$^b$ are each independently hydrogen; lower alkyl, lower cycloalkyl, lower alkenyl, lower alkynyl wherein these substituents are optionally substituted with halogen;

R$^a$ and R$^b$ taken together with the nitrogen atom to which they are attached, form phthalimide R² is, each independently, hydrogen, halogen; lower alkyl, lower alkoxy wherein these substituents are optionally substituted with halogen, R³ is hydrogen; lower alkyl, lower cycloalkyl which is optionally substituted with halogen or oxo; lower alkyl-sulfonyl, or aryl-sulfonyl;

R⁴ and R⁵ are each independently hydrogen, lower alkyl, lower alkenyl, lower alkynyl, hydroxyl, amino optionally protected with an appropriate protective group, R⁴ and R⁵ taken together with the carbon atom to which they are attached, form carbonyl (C=O), hydrazone (C=N—NR$^c$R$^d$), R$^c$ and R$^d$ is hydrogen and benzyl;

n is 0 to 6, m is 0 to 2 or racemate, enantiomer, diastereomer, mixture thereof, or pharmaceutically acceptable salt thereof.

4. The compound of formula I according to claim 1, selected from the group consisting of: (2'S,6'R)-6'-Propyl-5',6'-dihydrospiro[indoline-3,2'-pyran)-2,4'(3'H)-dione, (2'S,6'S)-6'-Propyl-5',6'-dihydrospiro[indoline-3,2'-pyran)-2,4'(3'H)-dione, (2'R,6'S)-6'-Propyl-5',6'-dihydrospiro[indoline-3,2'-pyran]-2,4'(3'H)-dione, (2'R,6'R)-6'-Propyl-5',6'-dihydrospiro[indoline-3,2'-pyran)-2,4'(3'H)-dione, (2'S,6'R)-4-chloro-6'-propyl-5',6'-dihydrospiro[indoline-3,2'-pyran]-2,4'(3'H)-dione, (2'S,6'S)-4-chloro-6'-propyl-5',6'-dihydrospiro[indoline-3,2'-pyran]-2,4'(3'H)-dione, (2'R,6'S)-4-chloro-6'-propyl-5',6'-dihydrospiro[indoline-3,2'-pyran]-2,4'(3'H)-dione, (2'R,6'R)-4-chloro-6'-propyl-5',6'-dihydrospiro[indoline-3,2'-pyran]-2,4'(3'H)-dione, (2'S,6'R)-4-bromo-6'-propyl-5',6'-dihydrospiro[indoline-3,2'-pyran]-2,4'(3'H)-dione, (2'S,6'S)-4-bromo-6'-propyl-5',6'-dihydrospiro[indoline-3,2'-pyran]-2,4'(3'H)-dione, (2'R,6'S)-4-bromo-6'-propyl-5',6'-dihydrospiro[indoline-3,2'-pyran]-2,4'(3'H)-dione, (2'R,6'R)-4-bromo-6'-propyl-5',6'-dihydrospiro[indoline-3,2'-pyran]-2,4'(3'H)-dione, (2'S,6'R)-5-methyl-6'-propyl-5',6'-dihydrospiro[indoline-3,2'-pyran]-2,4'(3'H)-dione, (2'S,6'S)-5-methyl-6'-propyl-5',6'-dihydrospiro[indoline-3,2'-pyran]-2,4'(3'H)-dione, (2'R,6'S)-5-methyl-6'-propyl-5',6'-dihydrospiro[indoline-3,2'-pyran]-2,4'(3'H)-dione, (2'R,6'R)-5-methyl-6'-propyl-5',6'-dihydrospiro[indoline-3,2'-pyran]-2,4'(3'H)-dione, (2'S,6'R)-5-bromo-6'-propyl-5',6'-dihydrospiro[indoline-3,2'-pyran]-2,4'(3'H)-dione, (2'S,6'S)-5-bromo-6'-propyl-5',6'-dihydro spiro[indoline-3,2'-pyran]-2,4'(3'H)-dione, (2'R,6'S)-5-bromo-6'-propyl-5',6'-dihydrospiro[indoline-3,2'-pyran]-2,4'(3'H)-dione, (2'R,6'R)-5-bromo-6'-propyl-5',6'-dihydrospiro[indoline-3,2'-pyran]-2,4'(3'H)-dione, (2'S,6'R)-6-chloro-6'-propyl-5',6'-dihydrospiro[indoline-3,2'-pyran]-2,4'(3'H)-dione, (2'S,6'S)-6-chloro-6'-propyl-5',6'-dihydrospiro[indoline-3,2'-pyran]-2,4'(3'H)-dione, (2'R,6'S)-6-chloro-6'-propyl-5',6'-dihydrospiro[indoline-3,2'-pyran]-2,4'(3'H)-dione, (2'R,6'R)-6-chloro-6'-propyl-5',6'-dihydrospiro[indoline-3,2'-pyran]-2,4'(3'H)-dione, (2'S,6'R)-6'-hexyl-5',6'-dihydrospiro[indoline-3,2'-pyran]-2,4'(3'H)-dione, (2'S,6'S)-6'-hexyl-5',6'-dihydrospiro[indoline-3,2'-pyran]-2,4'(3'H)-dione, (2'R,6'S)-6'-hexyl-5',6'-dihydrospiro[indoline-3,2'-pyran]-2,4'(3'H)-dione, (2'R,6'R)-6'-hexyl-5',6'-dihydrospiro[indoline-3,2'-pyran]-2,4'(3'H)-dione, (2'S,6'S)-6'-isopropyl-5',6'-dihydrospiro[indoline-3,2'-pyran]-2,4'(3'H)-dione, (2'S,6'R)-6'-isopropyl-5',6'-dihydrospiro[indoline-3,2'-pyran]-2,4'(3'H)-dione, (2'R,6'R)-6'-isopropyl-5',6'-dihydrospiro[indoline-3,2'-pyran]-2,4'(3'H)-dione, (2'R,6'S)-6'-isopropyl-5',6'-dihydrospiro[indoline-3,2'-pyran]-2,4'(3'H)-dione, (2'S,6'R)-6'-phenethyl-5',6'-dihydrospiro[indoline-3,2'-pyran]-2,4'(3'H)-dione, (2'S,6'S)-6'-phenethyl-5',6'-dihydrospiro[indoline-3,2'-pyran]-2,4'(3'H)-dione, (2'R,6'S)-6'-phenethyl-5',6'-dihydrospiro[indoline-3,2'-pyran]-2,4'(3'H)-dione, (2'R,6'R)-6'-phenethyl-5',6'-dihydrospiro[indoline-3,2'-pyran]-2,4'(3'H)-dione, (2'S,6'R)-6'-(but-3-yn-1-yl)-5',6'-dihydrospiro[indoline-3,2'-pyran]-2,4'(3'H)-dione, (2'S,6'S)-6'-(but-3-yn-1-yl)-5',6'-dihydrospiro[indoline-3,2'-pyran]-2,4'(3'H)-dione, (2'R,6'S)-6'-(but-3-yn-1-yl)-5',6'-dihydrospiro[indoline-3,2'-pyran]-2,4'(3'H)-dione, (2'R,6'R)-6'-(but-3-yn-1-yl)-5',6'-dihydrospiro[indoline-3,2'-pyran]-2,4'(3'H)-dione, (2'S,6'R)-6'-(but-3-en-1-yl)-5',6'-dihydrospiro[indoline-3,2'-pyran]-2,4'(3'H)-dione, (2'S,6'S)-6'-(but-3-en-1-yl)-5',6'-dihydrospiro[indoline-3,2'-pyran]-2,4'(3'H)-dione, (2'R,6'S)-6'-(but-3-en-1-yl)-5',6'-dihydrospiro[indoline-3,2'-pyran]-2,4'(3'H)-dione, (2'R,6'R)-6'-(but-3-en-1-yl)-5',6'-dihydrospiro[indoline-3,2'-pyran]-2,4'(3'H)-dione, (2'S,6'R)-6'-(2-(1,3-dioxoisoindolin-2-yl)ethyl)-5',6'-dihydrospiro[indoline-3,2'-pyran]-2,4'(3'H)-dione, (2'S,6'S)-6'-(2-(1,3-dioxoisoindolin-2-yl)ethyl)-5',6'-dihydrospiro[indoline-3,2'-pyran]-2,4'(3'H)-dione, (2'R,6'S)-6'-(2-(1,3-dioxoisoindolin-2-yl)ethyl)-5',6'-dihydrospiro[indoline-3,2'-pyran]-2,4'(3'H)-dione, (2'R,6'R)-6'-(2-(1,3-dioxoisoindolin-2-yl)ethyl)-5',6'-dihydrospiro[indoline-3,2'- pyran]-2,4'(3'H)-dione, (2'S,6'R)-6'-(3-((tert-butyldimethylsilyl)oxy)propyl)-5',6'-dihydrospiro[indoline-3,2'-pyran]-2,4'(3'H)-dione, (2'S,6'S)-6'-(3-((tert-butyldimethylsilyl)oxy)propyl)-5',6'-dihydrospiro[indoline-3,2'-pyran]-2,4'(3'H)-dione, (2'R,6'S)-6'-(3-((tert-butyldimethylsilyl)oxy)propyl)-5',6'-dihydrospiro[indoline-3,2'-pyran]-2,4'(3'H)-dione, (2'R,6'R)-6'-(3-((tert-butyldimethylsilyl)oxy)propyl)-5',6'-dihydrospiro[indoline-3,2'-pyran]-2,4'(3'H)-dione, (2'S,6'R)-6'-(3-chloropropyl)-5',6'-dihydrospiro[indoline-3,2'-pyran]-2,4'(3'H)-dione, (2'S,6'S)-6'-(3-chloropropyl)-5',6'-dihydrospiro[indoline-3,2'-pyran]-2,4'(3'H)-dione, (2'R,6'S)-6'-(3-chloropropyl)-5',6'-dihydrospiro[indoline-3,2'-pyran]-2,4'(3'H)-dione, (2'R,6'R)-6'-(3-chloropropyl)-5',6'-dihydrospiro[indoline-3,2'-pyran]-2,4'(3'H)-dione, (2'R,6'R)-6'-phenyl-5',6'-dihydrospiro[indoline-3,2'-pyran]-2,4'(3'H)-dione, (2'R,6'S)-6'-phenyl-5',6'-dihydrospiro[indoline-3,2'-pyran]-2,4'(3'H)-dione, (2'S,6'S)-6'-phenyl-5',6'-dihydrospiro[indoline-3,2'-pyran]-2,4'(3'H)-dione, (2'S,6'R)-6'-phenyl-5',6'-dihydrospiro[indoline-3,2'-pyran]-2,4'(3'H)-dione, (2'S,4'R,6'R)-4'-hydroxy-6'-propyl-3',4',5',6'-tetrahydrospiro[indoline-3,2'-pyran]-2-one, (2'S,4'R,6'S)-4'-hydroxy-6'-propyl-3',4',5',6'-tetrahydrospiro[indoline-3,2'-pyran]-2-one, (2'S,4'S,6'R)-4'-hydroxy-6'-propyl-3',4',5',6'-tetrahydrospiro[indoline-3,2'-pyran]-2-one, (2'R,4'R,6'R)-4'-hydroxy-6'-propyl-3',4',5',6'-tetrahydrospiro[indoline-3,2'-pyran]-2-one, (2'R,4'S,6'S)-4'-hydroxy-6'-propyl-3',4',5',6'-tetrahydrospiro[indoline-3,2'-pyran]-2-one, (2'R,4'S,6'R)-4'-hydroxy-6'-propyl-3',4',5',6'-tetrahydrospiro[indoline-3,2'-pyran]-2-one, (2'R,4'R,6'S)-4'-hydroxy-6'-propyl-3',4',5',6'-tetrahydrospiro[indoline-3,2'-pyran]-2-one, (2'S,4'S,6'S)-4'-hydroxy-6'-propyl-3',4',5',6'-tetrahydrospiro[indoline-3,2'-pyran]-2-one, (2'S,4'R,6'R)-4'-(benzylamino)-6'-propyl-3',4',5',6'-tetrahydrospiro[indoline-3,2'-pyran]-2-one, (2'S,4'R,6'S)-4'-(benzylamino)-6'-propyl-3',4',5',6'-tetrahydrospiro[indoline-3,2'-pyran]-2-one, (2'S,4'S,6'R)-4'-(benzylamino)-6'-propyl-3',4',5',6'-tetrahydrospiro[indoline-3,2'-pyran]-2-one, (2'R,4'R,6'R)-4'-(benzylamino)-6'-propyl-3',4',5',6'-tetrahydrospiro[indoline-3,2'-pyran]-2-one, (2'R,4'S,6'S)-4'-(benzylamino)-6'-propyl-3',4',5',6'-tetrahydrospiro[indoline-3,2'-pyran]-2-one, (2'R,4'S,6'R)-4'-(benzylamino)-6'-propyl-3',4',5',6'-tetrahydrospiro[indoline-3,2'-pyran]-2-one, (2'R,4'R,6'S)-4'-(benzylamino)-6'-propyl-3',4',5',6'-tetrahydrospiro[indoline-3,2'-pyran]-2-one, (2'S,4'S,6'S)-4'-(benzylamino)-6'-propyl-3',4',5',6'-tetrahydrospiro[indoline-3,2'-pyran]-2-one, (2'S,4'R,6'R)-4'-allyl-4'-hydroxy-6'-propyl-3',4',5',6'-tetrahydrospiro[indoline-3,2'-pyran]-2-one, (2'S,4'R,6'S)-4'-allyl-4'-hydroxy-6'-propyl-3',4',5',6'-tetrahydrospiro[indoline-3,2'-pyran]-2-one, (2'S,4'S,6'R)-4'-allyl-4'-hydroxy-6'-propyl-3',4',5',6'-tetrahydrospiro[indoline-3,2'-pyran]-2-one, (2'R,4'R,6'R)-4'-allyl-4'-hydroxy-6'-propyl-3',4',5',6'-tetrahydrospiro[indoline-3,2'-pyran]-2-one, (2'R,4'S,6'S)-4'-allyl-4'-hydroxy-6'-propyl-3',4',5',6'-tetrahydrospiro[indoline-3,2'-pyran]-2-one, (2'R,4'S,6'R)-4'-allyl-4'-hydroxy-6'-propyl-3',4',5',6'-tetrahydrospiro[indoline-3,2'-pyran]-2-one, (2'R,4'R,6'S)-4'-allyl-4'-hydroxy-6'-propyl-3',4',5',6'-tetrahydrospiro[indoline-3,2'-pyran]-2-one, (2'S,4'S,6'S)-4'-allyl-4'-hydroxy-6'-propyl-3',4',5',6'-tetrahydrospiro[indoline-3,2'-pyran]-2-one, 4-Methyl-N'-((2'S,6'R)-2-oxo-6'-propyl-5',6'-dihydrospiro[indoline-3,2'-pyran]-4'(3'H)-ylidene)benzenesulfonohydrazide, 4-Methyl-N'-((2'S,6'S)-2-oxo-6'-propyl-5',6'-dihydrospiro[indoline-3,2'-pyran]-4'(3'H)-ylidene)benzenesulfonohydrazide, 4-Methyl-N'-((2'R,6'S)-2-oxo-6'-propyl-5',6'-dihydrospiro[indoline-3,2'-pyran]-4'(3'H)-ylidene)benzenesulfonohydrazide, and 4-Methyl-N'-((2'R,6'R)-2-oxo-6'-propyl-5',6'-dihydrospiro[indoline-3,2'-pyran]-4'(3'H)-ylidene)benzenesulfonohydrazide, or pharmaceutically acceptable salts thereof.

5. A process for preparing a compound of formula II:

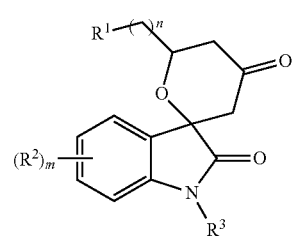

II wherein $R^1$, $R^2$, $R^3$, n, m is as defined in claim 1, or stereoisomers thereof, which process comprises reacting a compound of formula III:

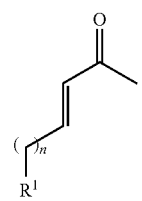

III wherein $R^1$ is as defined in the above;

with a compound of formula IV:

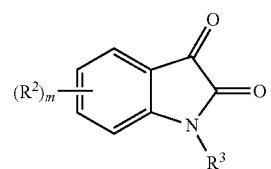

IV wherein $R^2$, $R^3$, m are as defined in the above;

in the presence of at least one amine selected from the group consisting of the following compounds represented by formulae A, B, C, D, E, F, G, H, and stereoisomers thereof and in the presence of at least one acid selected from the group consisting of the following compounds represented by formulae I, J, K, L, M, N, and stereoisomers thereof, and with or without additive O or molecular sieves 4A.

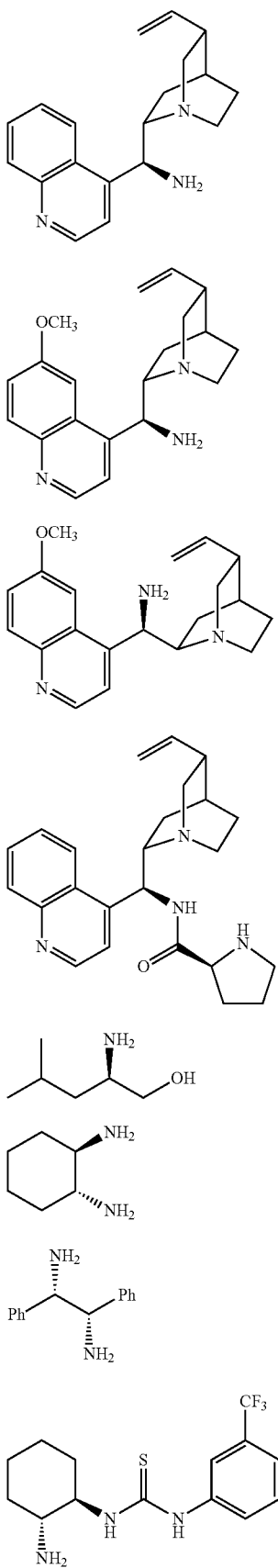

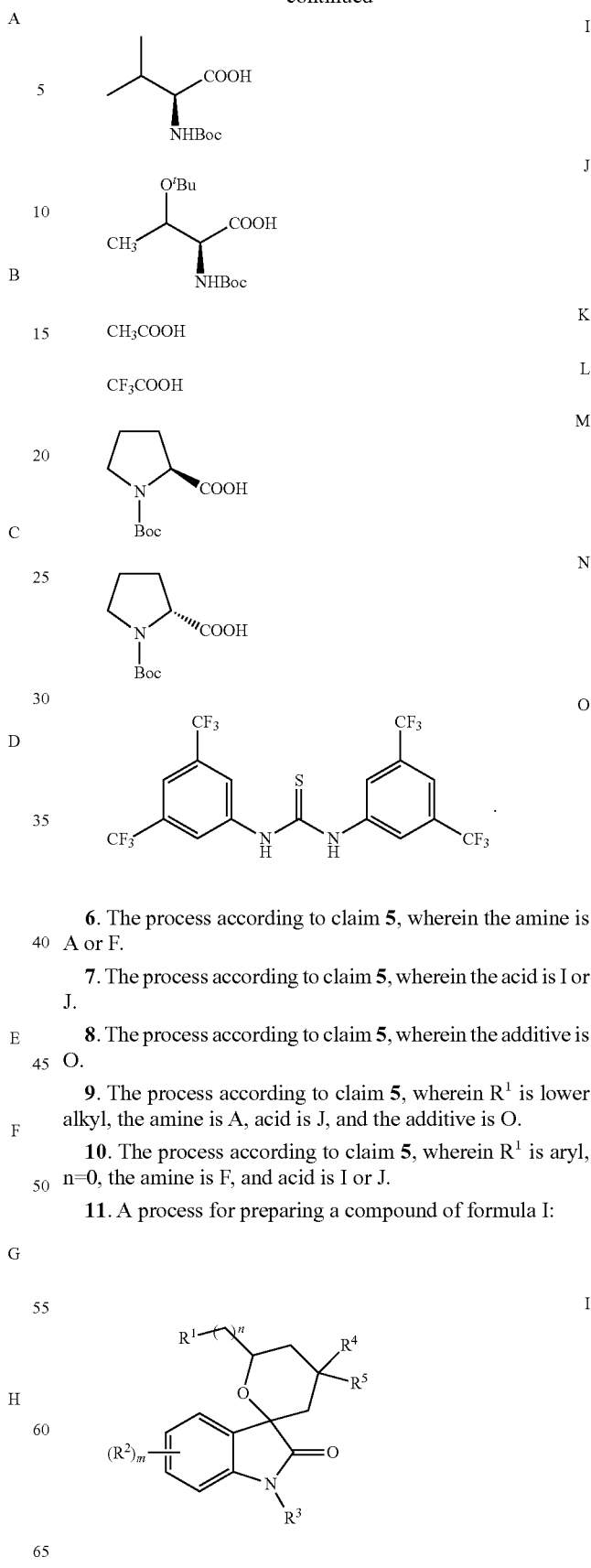

6. The process according to claim 5, wherein the amine is A or F.

7. The process according to claim 5, wherein the acid is I or J.

8. The process according to claim 5, wherein the additive is O.

9. The process according to claim 5, wherein $R^1$ is lower alkyl, the amine is A, acid is J, and the additive is O.

10. The process according to claim 5, wherein $R^1$ is aryl, n=0, the amine is F, and acid is I or J.

11. A process for preparing a compound of formula I:

wherein $R^1$ to $R^5$, m, and n are as defined in claim 1, which process comprises
a) reduction of carbonyl moiety of reacting a compound of formula II:

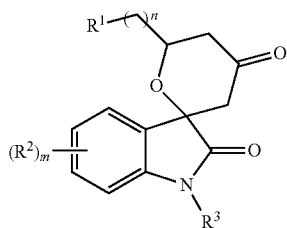

wherein $R^1$, $R^2$, $R^3$, m and n are as defined in claim 1,
b) reductive amination of carbonyl moiety of a compound of formula II as defiened above,
c) nucleophilic addition of carbonyl moiety of a compound of formula II as defiened above,
d) oximation of carbonyl moiety of a compound of formula II as defiened above,
e) hydrazination of carbonyl moiety of a compound of formula II as defiened above, or
f) acetalization of carbonyl moiety of a compound of formula II as defiened above.

12. A process for preparing a compound of formula I

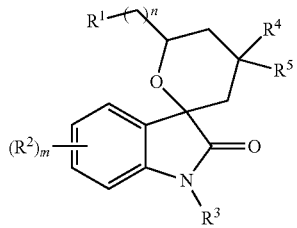

wherein $R^1$ to $R^5$, m and n are as defined in claim 1,
which process comprises
a) alkylation of indole nitrogen of a compound of formula I':

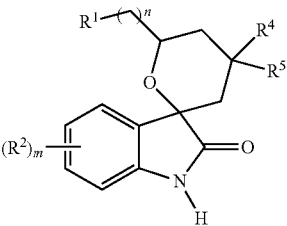

wherein $R^1$, $R^2$, $R^4$, $R^5$ m and n are as defined in claim 1,
b) amidation of indole nitrogen of a compound of formula I' as defiened above:
c) sulfonamidation of indole nitrogen of a compound of formula I' as defiened above.

13. A pharmaceutical composition comprising a compound of formula I according to claim 1, and a pharmaceutically acceptable adjuvant.

14. The pharmaceutical composition according to claim 13 for the treatment of proliferative diseases.

\* \* \* \* \*